(12) United States Patent
Mahulikar et al.

(10) Patent No.: US 8,742,130 B2
(45) Date of Patent: Jun. 3, 2014

(54) HYDRATE FORMS OF 1,2,4-TRIAZOLE, PROCESSES FOR MANUFACTURE THEREOF, AND COMPOSITIONS THEREOF

(71) Applicant: Fujifilm Planar Solutions, LLC, Adrian, MI (US)

(72) Inventors: Deepak Mahulikar, N. Kingstown, RI (US); Luling Wang, Mesa, AZ (US)

(73) Assignee: Fujifilm Planar Solutions, LLC, Adrian, MI (US)

( * ) Notice: Subject to any disclaimer, the term of this patent is extended or adjusted under 35 U.S.C. 154(b) by 0 days.

(21) Appl. No.: 13/666,257

(22) Filed: Nov. 1, 2012

(65) Prior Publication Data

US 2014/0121382 A1 May 1, 2014

(51) Int. Cl.
*C07D 249/08* (2006.01)

(52) U.S. Cl.
USPC ...................................... 548/262.2

(58) Field of Classification Search
None
See application file for complete search history.

(56) References Cited

PUBLICATIONS

Chemical Abstract Service (CAS) STN Registry Database No. (RN) 253171-14-1 [entered STN: Jan. 20, 2000].*
Ermakova et al. "Modification of Polyvinyl Chloride with Na(K) Salts of 1,2,4-Triazole and 1,2,3-Benzotriazole." Russian Journal of Applied Chemistry 2009, 82, 488-491.*

* cited by examiner

*Primary Examiner* — Samantha Shterengarts
*Assistant Examiner* — Amanda L Aguirre
(74) *Attorney, Agent, or Firm* — Ohlandt, Greeley, Ruggiero & Perle, LLP

(57) ABSTRACT

The present invention provides new hydrate forms of triazole, triazole alkaline salt, and alkali doped 1,2,4-triazole. The present invention also discloses processes for manufacturing new hydrate forms of triazole, triazole alkaline salt, and alkali-doped 1,2,4-triazole. The present invention also relates to compositions for different applications of new hydrate forms of triazole, triazole alkaline salt, and alkali doped 1,2, 4-triazole. In addition, the present invention provides co-crystal form of triazole with acid, and methods of preparing thereof.

8 Claims, 27 Drawing Sheets

HYDRATE FORMS OF 1,2,4-TRIAZOLE, PROCESSES FOR MANUFACTURE THEREOF, AND COMPOSITIONS THEREOF

BACKGROUND OF THE DISCLOSURE

1. Field of the Disclosure

The present disclosure relates to new hydrate and crystalline forms of triazole. More particularly, the present disclosure relates to hydrate and crystalline forms of 1,2,4-triazole, 1,2,4-triazole alkaline salt, alkali doped 1,2,4-triazole, and 1,2,4-triazole co-crystal with acid, processes for the manufacture thereof, and compositions thereof.

2. Description of the Related Art 1,2,4-triazole and its derivatives are used in pharmaceutical applications, material science, metal corrosion inhibitors, and herbicides. Various methods of synthesizing 1,2,4-triazole and its derivatives have been reported in the art.

Some organic and/or inorganic molecules can form a hydrate crystal, which might change physical or chemical properties of the molecules. In the pharmaceutical industry, for example, crystal forms of active pharmaceutical ingredients (API) can improve the stability, bioavailability and other performance factors of the API. Some poorly water-soluble drugs may show better dissolution rate by changing the physical state of the drug such as hydrates or crystalline forms.

However, hydrates can be very difficult to synthesize. There are no currently available or known 1,2,4-triazole hydrates, or processes for making the same. The present disclosure addresses this need

SUMMARY OF THE DISCLOSURE

The present invention provides new hydrate forms of 1,2,4-triazole, 1,2,4-triazole alkaline salt, and alkali doped 1,2,4-triazole. The present invention also discloses processes for manufacturing new hydrate forms of 1,2,4-triazole, 1,2,4-triazole alkaline salt, and alkali doped 1,2,4-triazole. The present invention also relates to compositions for different applications of new hydrate forms of 1,2,4-triazole, 1,2,4-triazole alkaline salt, and alkali doped 1,2,4-triazole. The present invention also provides a co-crystal form of 1,2,4-triazole with acid, and methods of preparing thereof.

BRIEF DESCRIPTION OF THE DRAWINGS

FIG. 1-b shows an expanded XRD spectrum of a 1,2,4-triazole hydrate sample described in Example 1.

FIG. 1-c shows a differential scanning calorimetry (DSC) curve of the 1,2,4-triazole hydrate sample described in Example 1.

FIG. 1-d shows a thermogravimetric analysis (TGA) and derivative TGA curves of the 1,2,4-triazole hydrate sample described in Example 1.

FIG. 1-e shows a Raman spectrum of the 1,2,4-triazole hydrate sample described in Example 1.

FIG. 2-b shows an expanded XRD spectrum of the 1,2,4-triazole hydrate sample described in Example 2.

FIG. 2-c shows a DSC curve of the 1,2,4-triazole hydrate sample described in Example 2.

FIG. 2-d shows TGA and derivative TGA curves of the 1,2,4-triazole hydrate sample described in Example 2.

FIG. 2-e shows a Raman spectrum of the 1,2,4-triazole hydrate sample described in Example 2.

FIG. 3-b shows an expanded XRD spectrum of the ammonium hydroxide doped 1,2,4-triazole hydrate sample described in Example 3.

FIG. 3-c shows a DSC curve of ammonium hydroxide doped 1,2,4-triazole hydrate sample described in Example 3.

FIG. 3-d shows TGA and derivative TGA curves of the ammonium hydroxide doped 1,2,4-triazole hydrate sample as described in Example 3.

FIG. 3-e shows a Raman spectrum of ammonium hydroxide doped 1,2,4-triazole hydrate sample describes in Example 3.

FIG. 4-b shows a DSC curve of the 1,2,4-triazole potassium salt hydrate sample as described in Example 4.

FIG. 4-c shows a Raman spectrum of the 1,2,4-triazole potassium salt hydrate sample describes in Example 4.

FIG. 5-b shows an expanded XRD spectrum of the KOH doped 1,2,4-triazole hydrate sample described in Example 5.

FIG. 5-c shows a DSC curve of the KOH doped 1,2,4-triazole hydrate sample described in Example 5.

FIG. 5-d shows a Raman spectrum of the KOH doped 1,2,4-triazole hydrate sample described in Example 5.

FIG. 6-b shows an expanded XRD spectrum of the KOH doped 1,2,4-triazole hydrate sample described in Example 6.

FIG. 6-c shows a DSC curve of the KOH doped 1,2,4-triazole hydrate sample described in Example 6.

FIG. 6-d shows a Raman spectrum of the KOH doped 1,2,4-triazole hydrate sample described in Example 6.

DETAILED DESCRIPTION OF THE DISCLOSURE

Figure 1A:
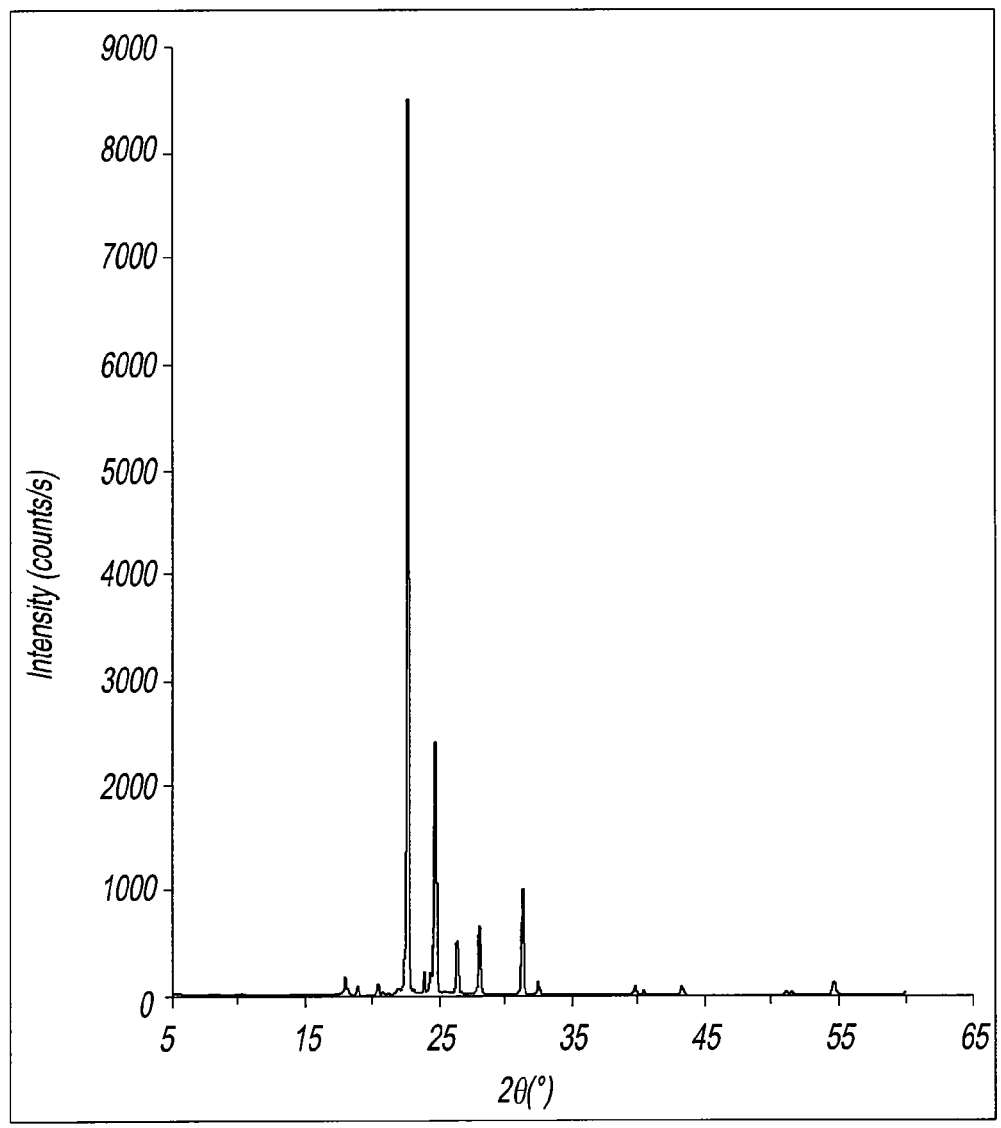
FIG. 1-a shows an x-ray diffraction (XRD) spectrum of the 1,2,4-triazole hydrate sample described in Example 1.
Figure 1B:
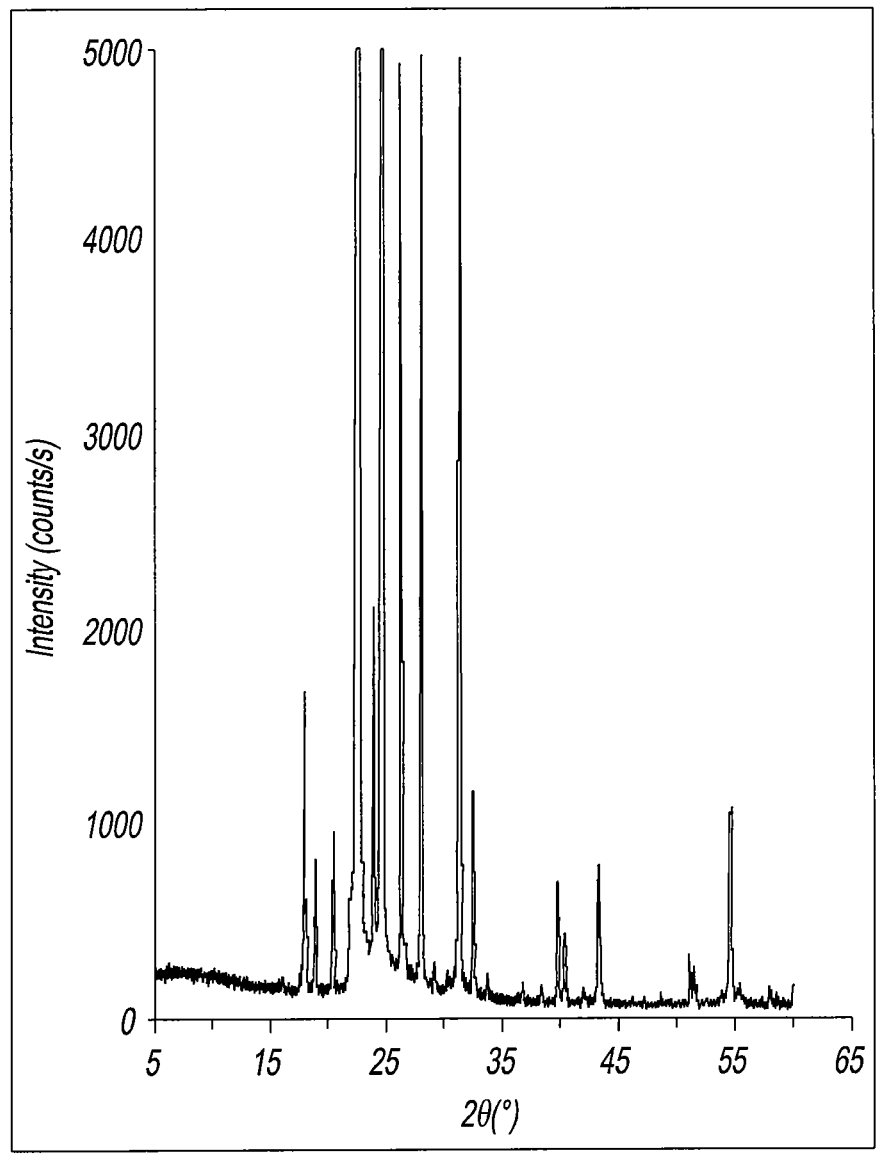
Figure 1C:
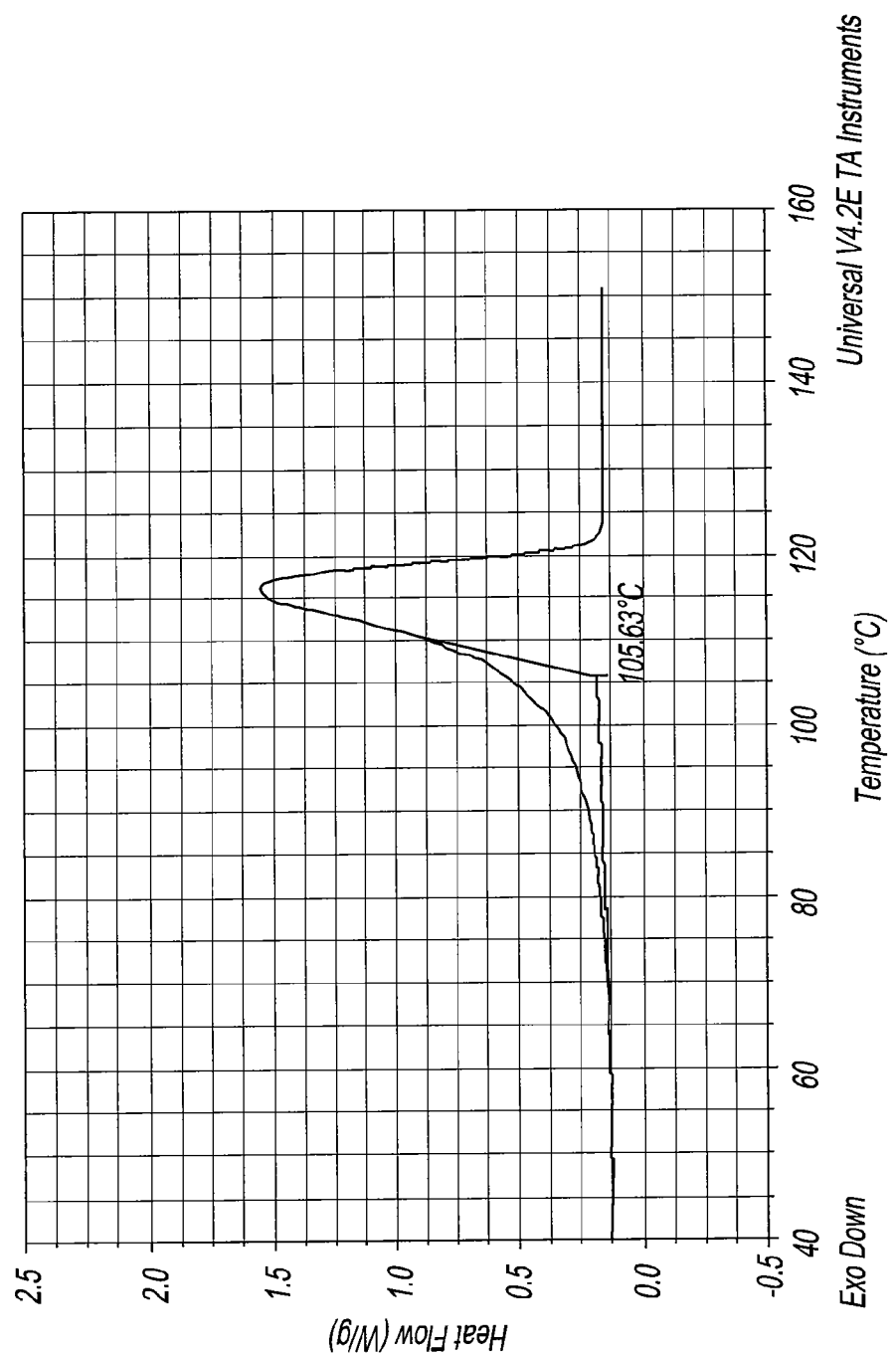
Figure 1D:
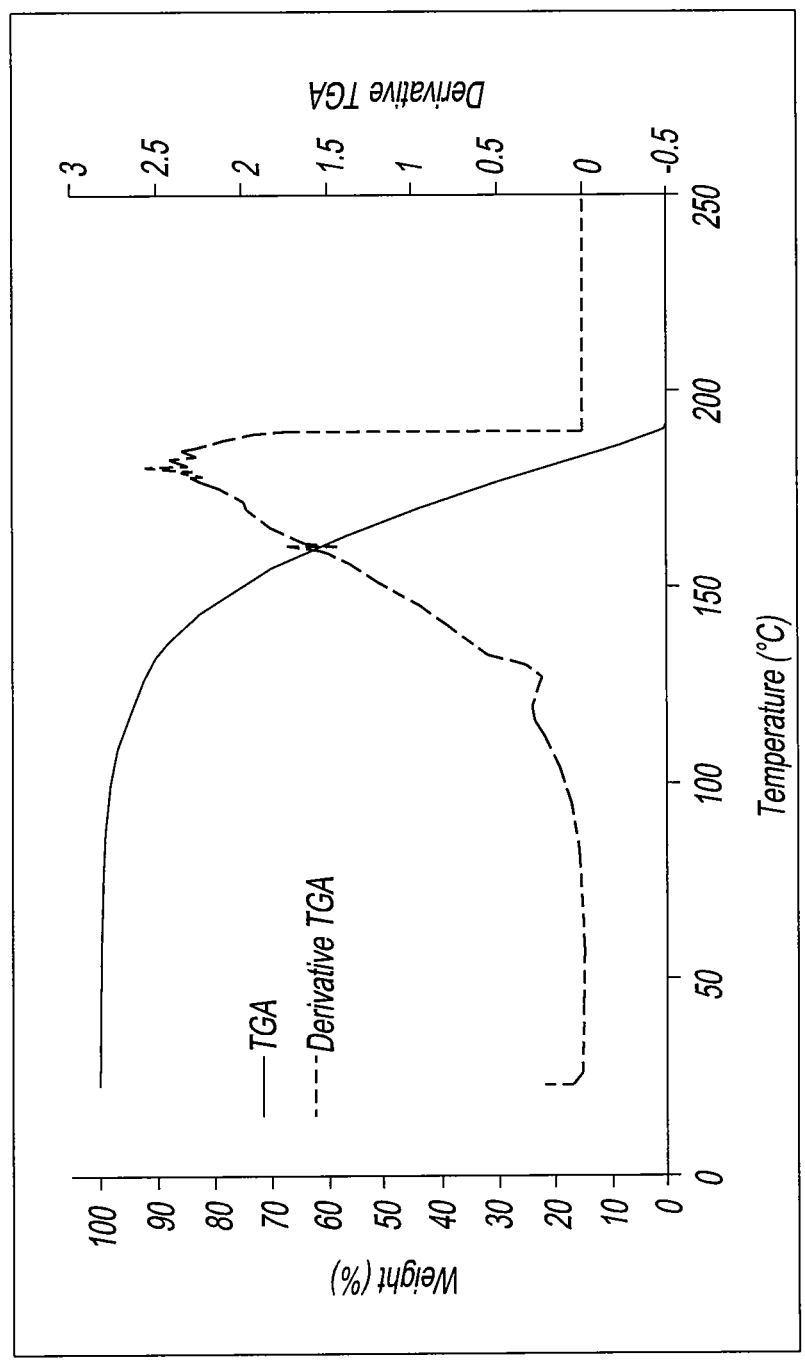
Figure 1E:
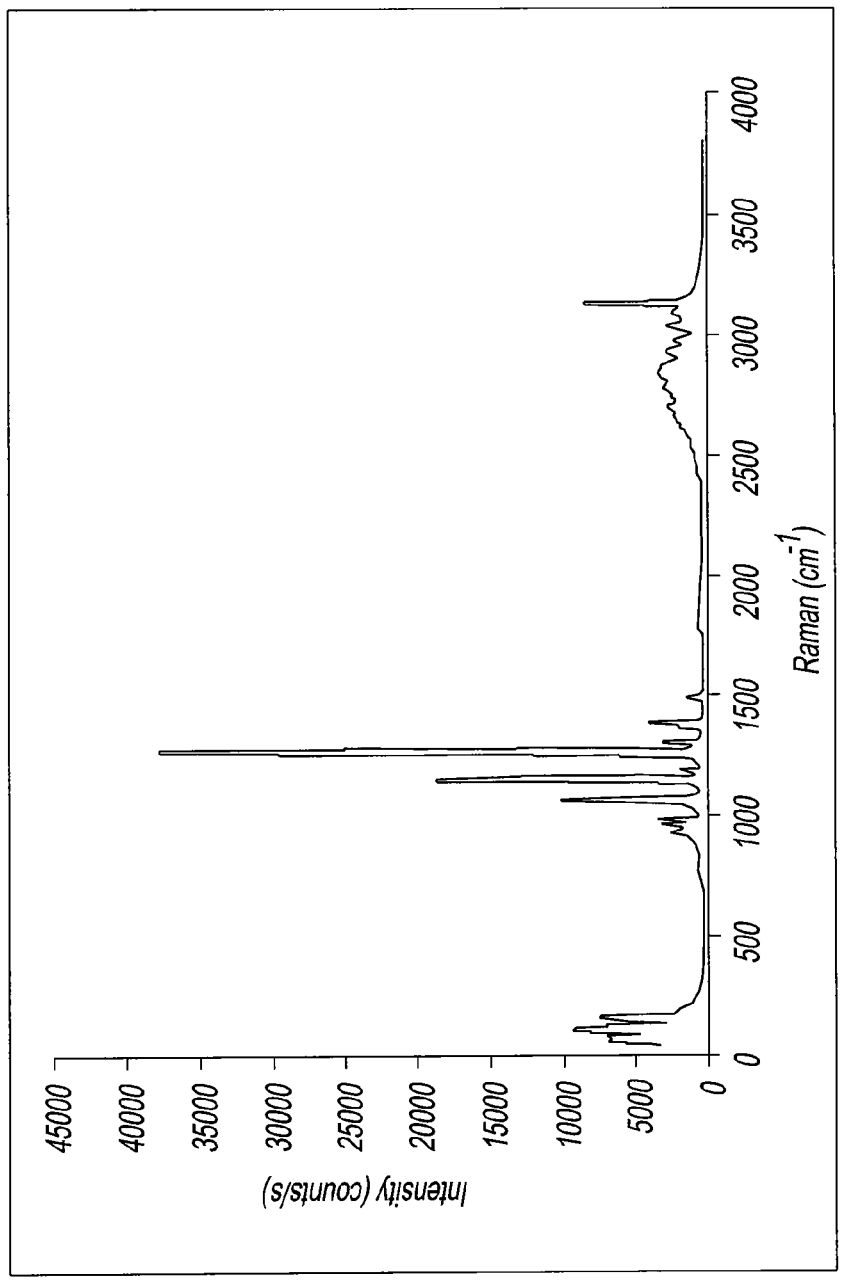
Figure 2A:
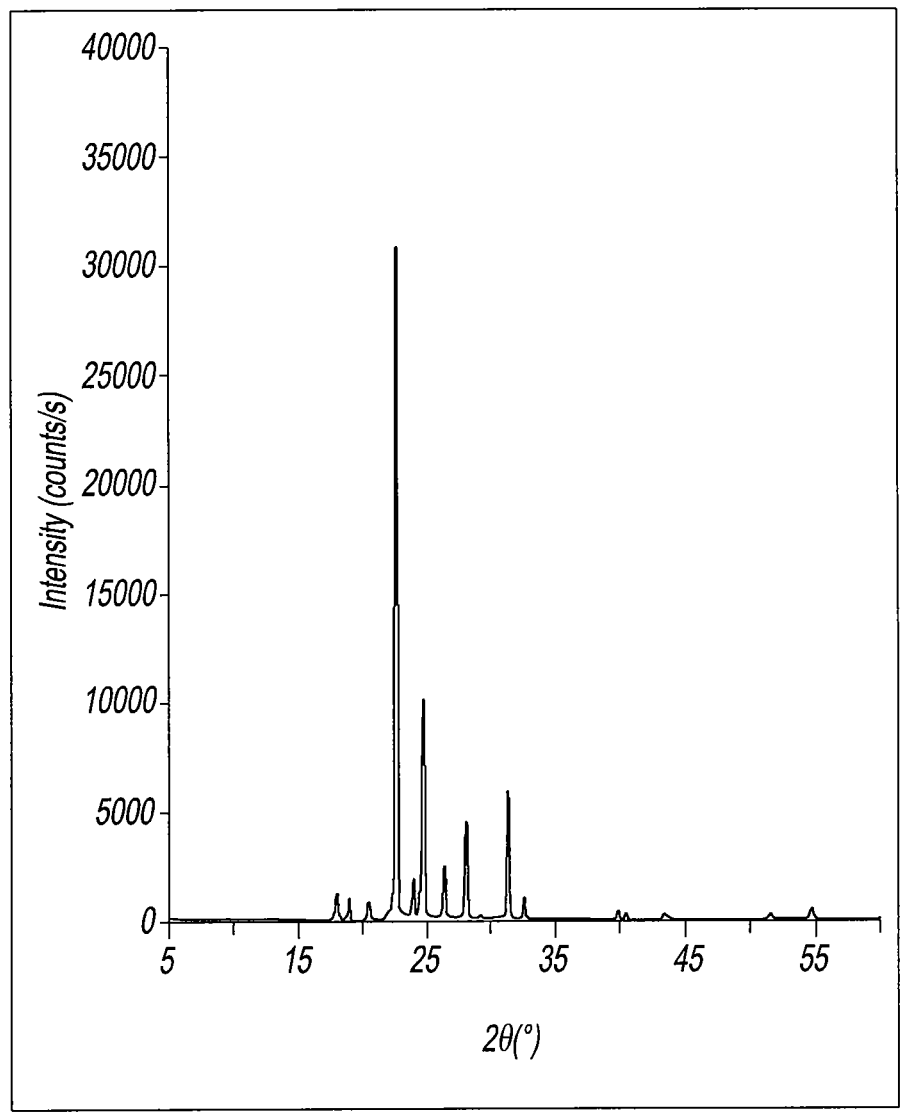
FIG. 2-a shows an XRD spectrum of the 1,2,4-triazole hydrate sample described in Example 2.
Figure 2B:
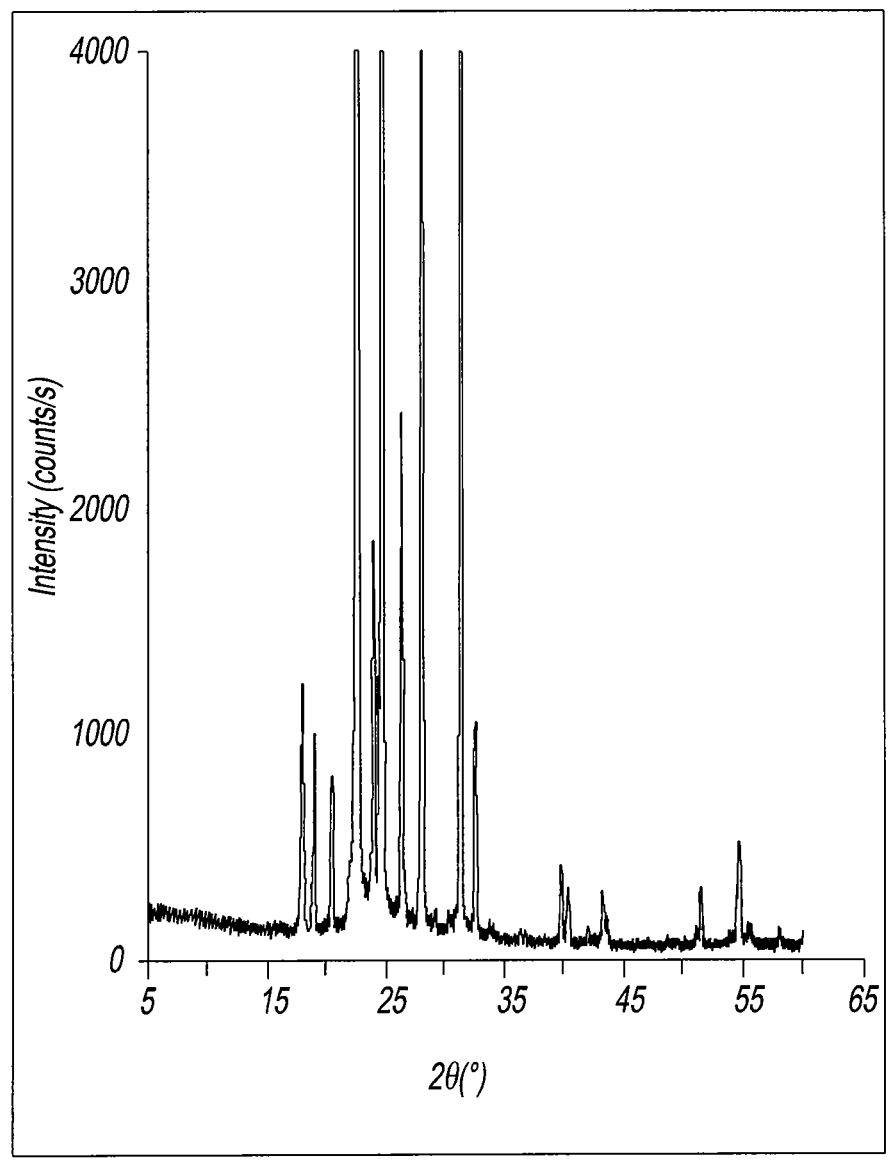
Figure 2C:
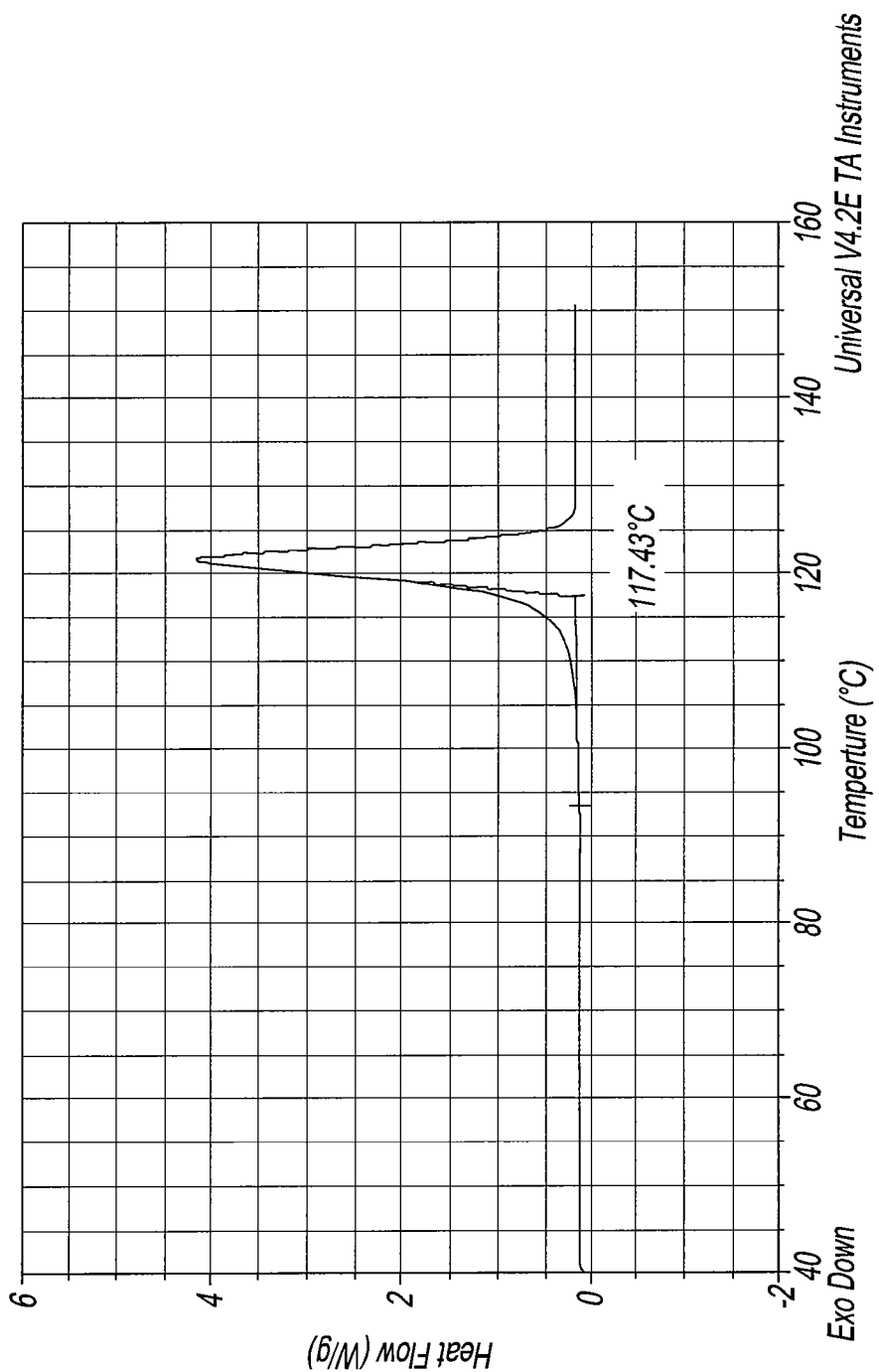
Figure 2D:
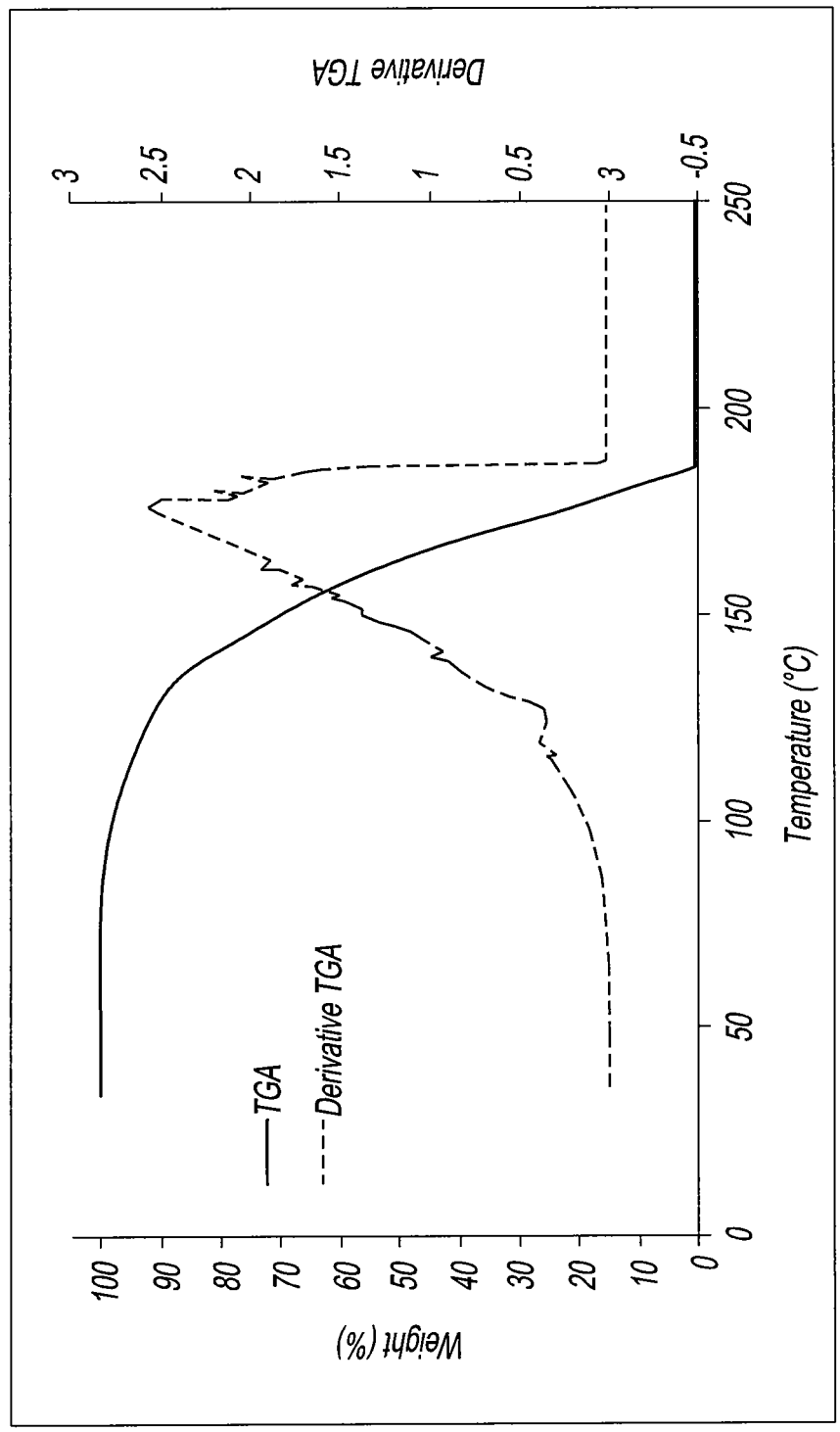
Figure 2E:
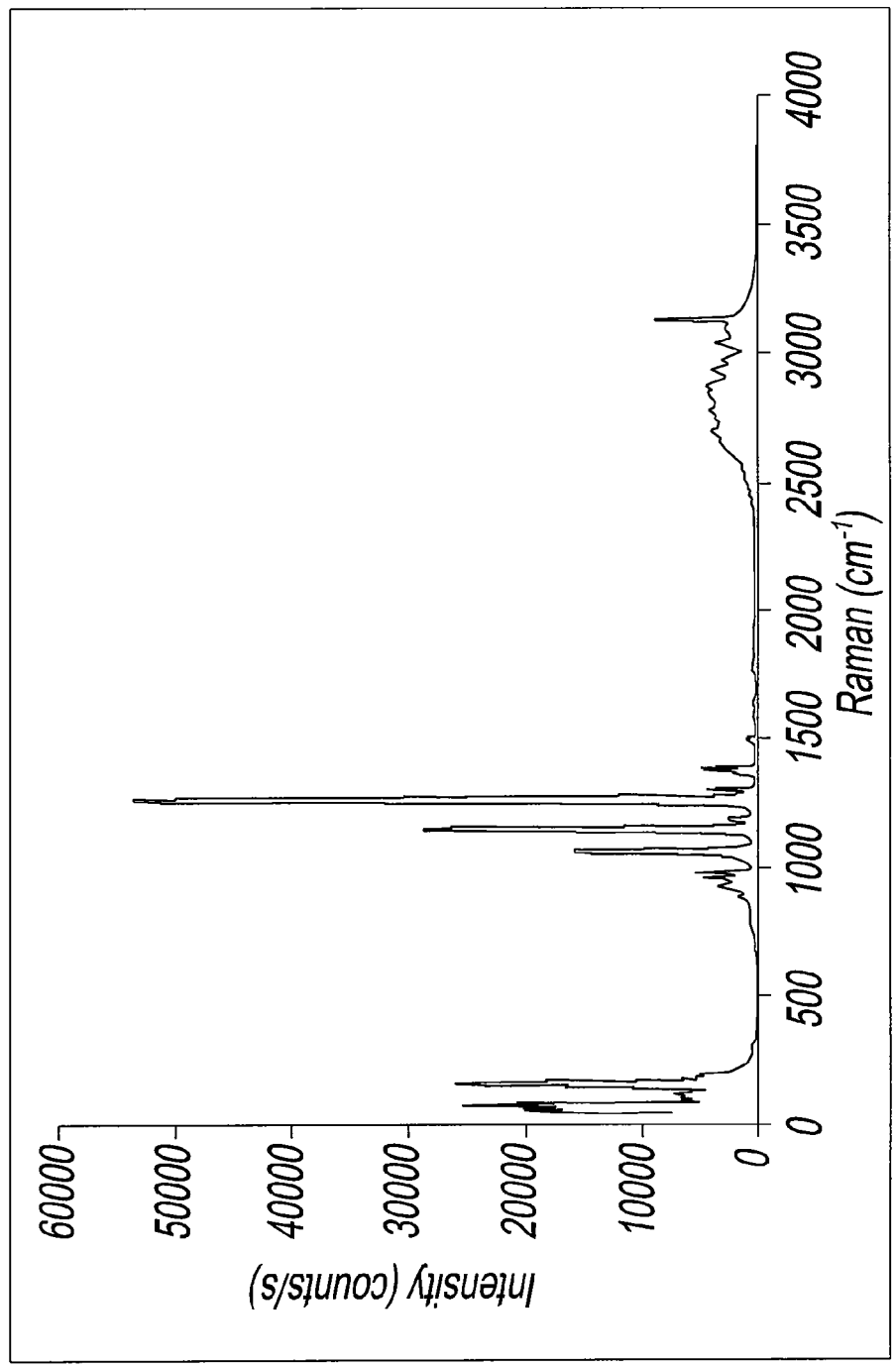
Figure 3A:
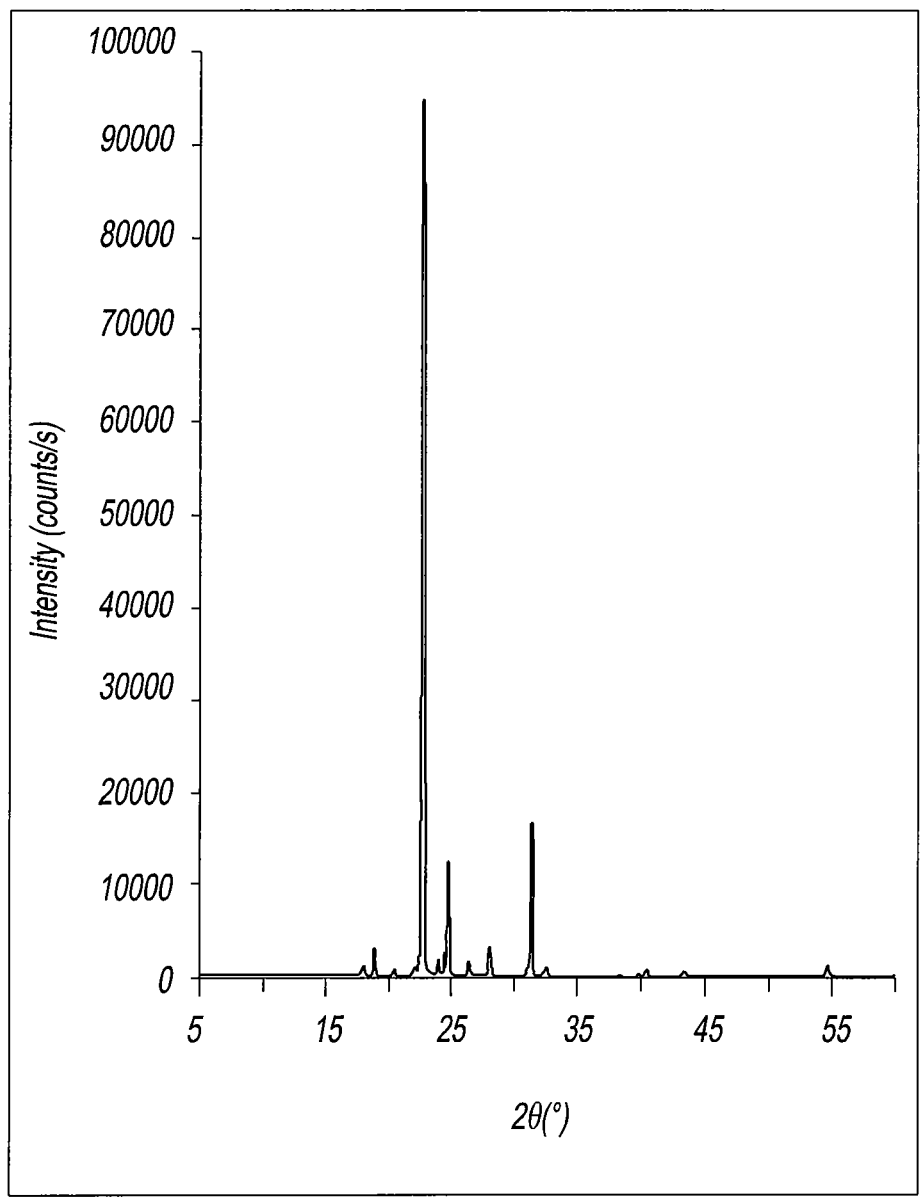
FIG. 3-a shows an XRD spectrum of the ammonium hydroxide doped 1,2,4-triazole hydrate sample described in Example 3.
Figure 3B:
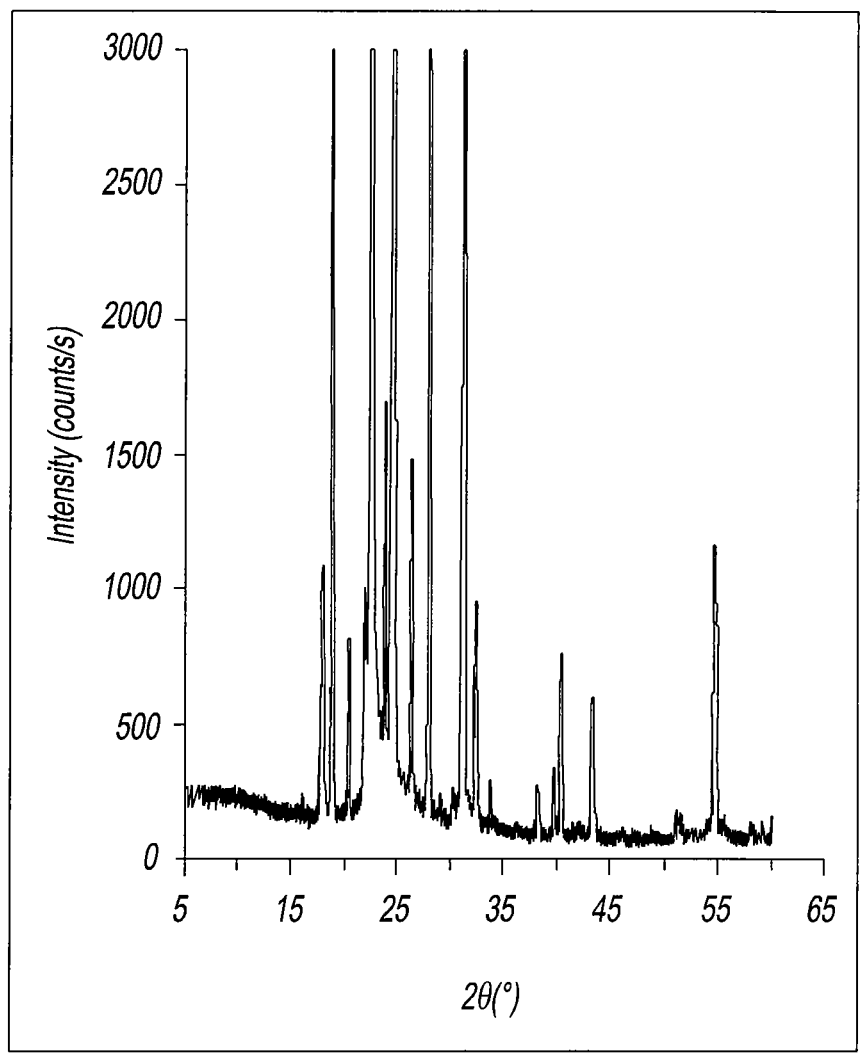
Figure 3C:
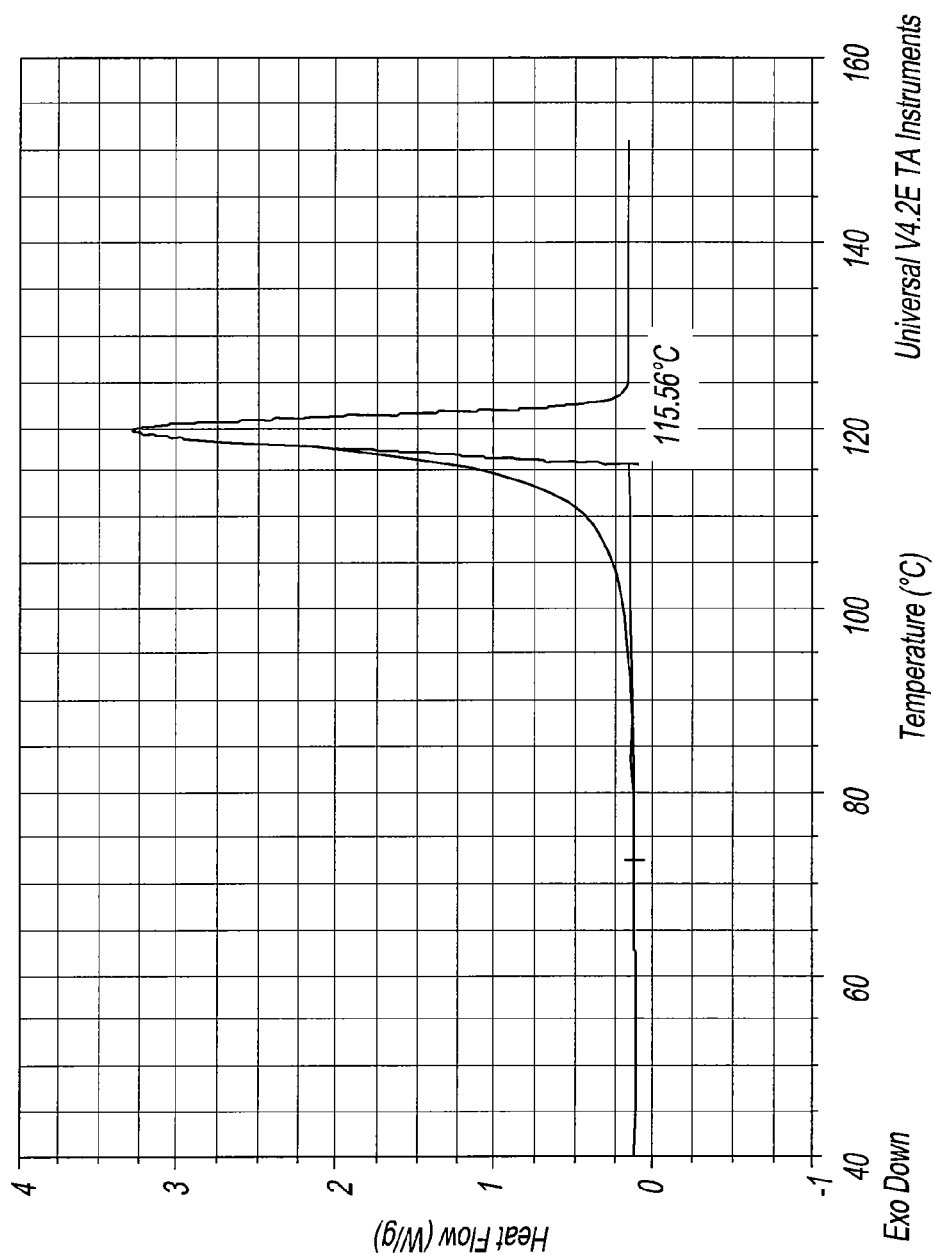
Figure 3D:
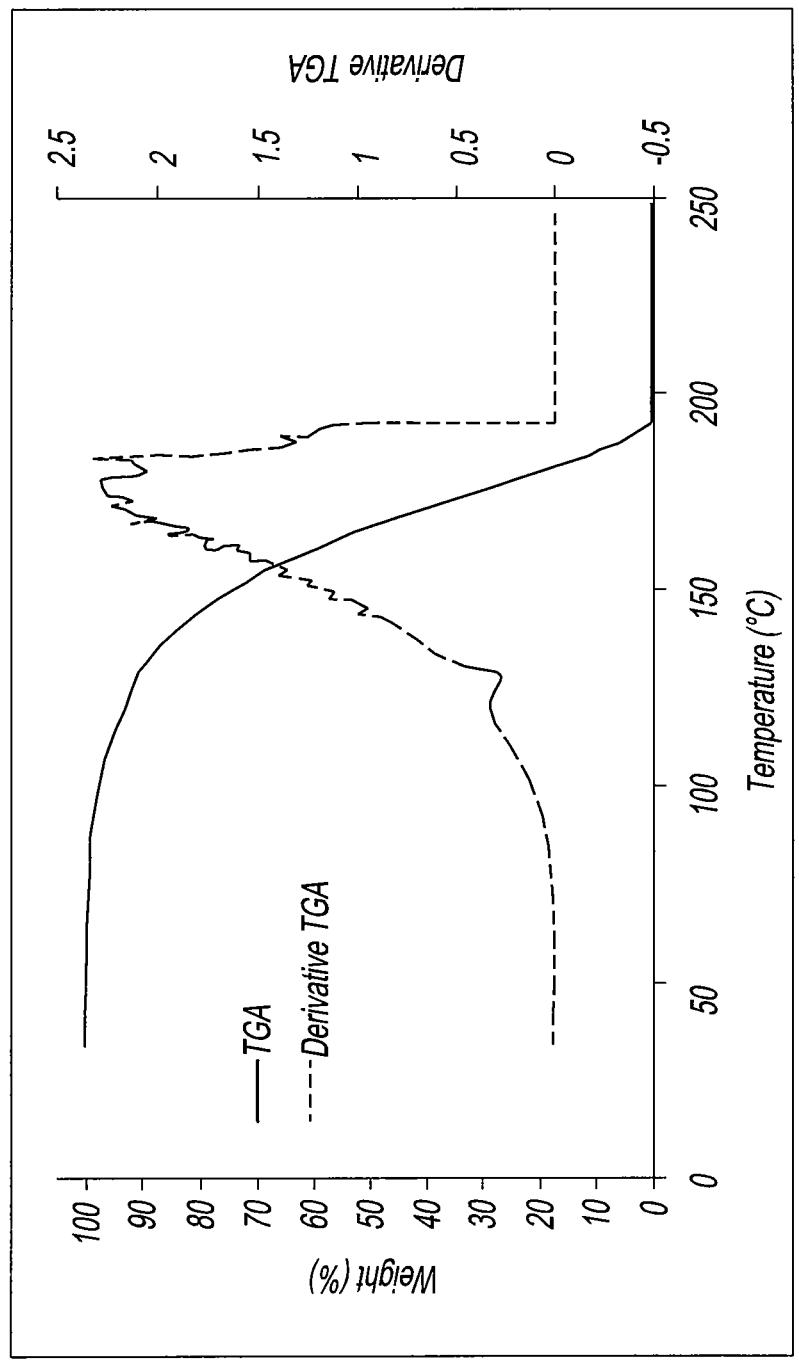
Figure 3E:
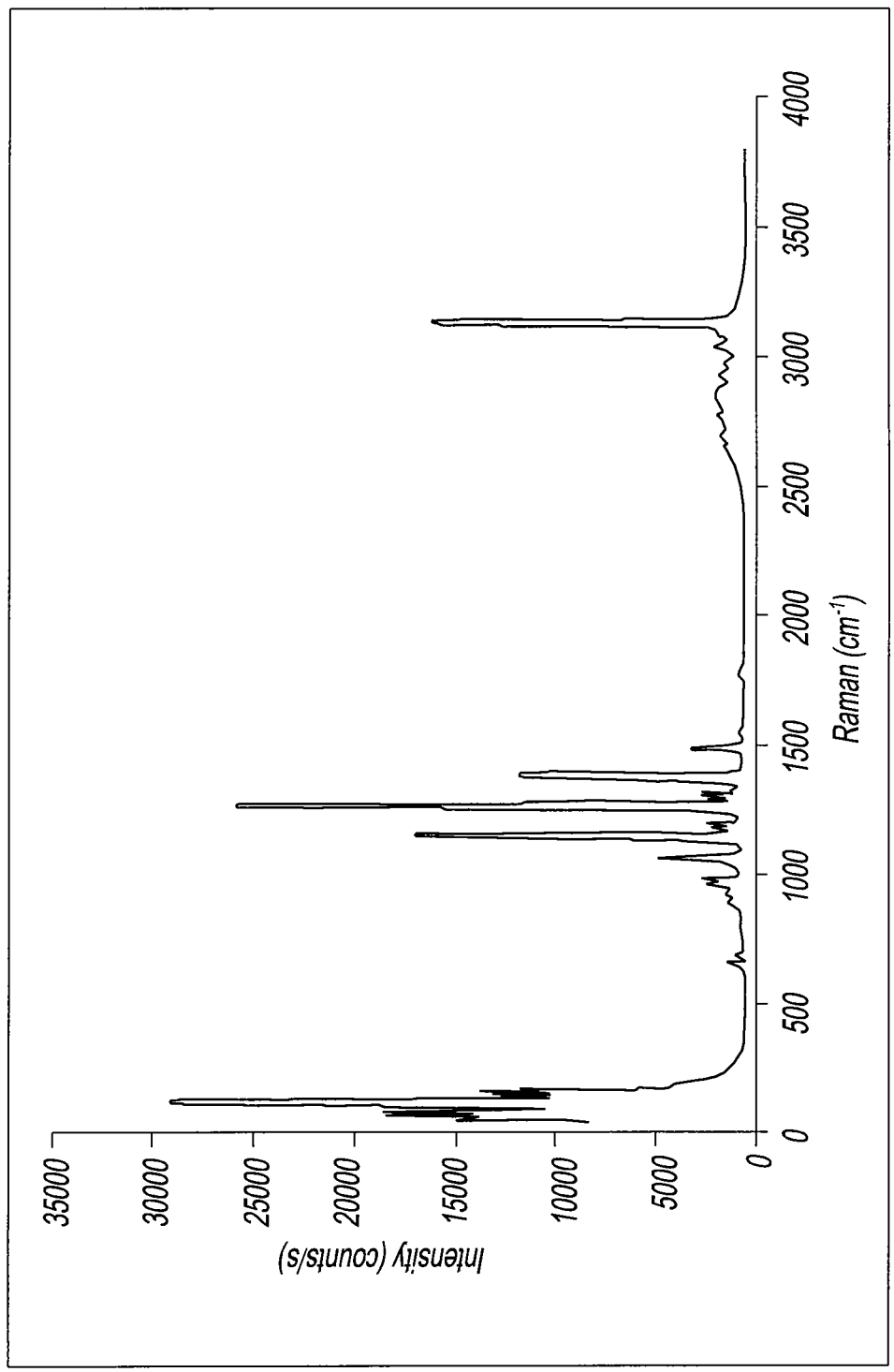

The present disclosure provides four novel forms of 1,2,4-triazole. The first three of these are hydrates of 1,2,4-triazole, 1,2,4-triazole alkaline salt and 1,2,4-triazole with alkali doping. The fourth is a co-crystal form of 1,2,4-triazole with acid. The present disclosure also provides processes for manufacturing each of these four forms of triazole, and compositions for using them. For ease of description in the present application, 1,2,4-triazole will be referred to simply as "triazole".

The hydrates and co-crystals of triazole described herein provide significant advantages for use in any number of compositions and applications. For example, hydrating and forming co-crystals of triazole can place it in a crystal form, which can make it less toxic. The hydrate and co-crystals can also have lower melting points than pure triazole, which can improve its solubility, and therefore stability. This can be very useful in applications such as chemical-mechanical polishing slurries. There are no triazole hydrates or co-crystals currently available, likely because hydrating a complex molecule such as triazole can be difficult.

In one embodiment, the hydrates of the present disclosure have the following formula (I):

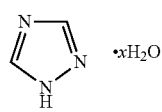

$$\text{(I)}$$

In another embodiment, the hydrates are alkaline doped triazole hydrates. Two examples of this embodiment are shown in formulas (II) and (III), in which the alkaline is ammonium hydroxide and potassium hydroxide, respectively.

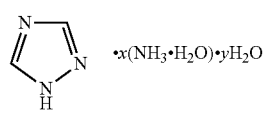

$$\text{(II)}$$

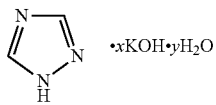

$$\text{(III)}$$

In another embodiment, the hydrates are alkali doped triazole hydrates generally having formula (IV):

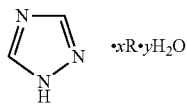

$$\text{(IV)}$$

In formula (IV), R can be any alkali group or molecule. In any of formulas (I)-(IV), x and y can be integers, or fractions thereof, and can be the same or different numbers.

As stated above, the fourth type of novel triazole of the present disclosure is the co-crystal form of triazole with acid.

The following are processes that can be used to make the triazole hydrates and co-crystals of the present disclosure.

In one embodiment, a Sample A is prepared by melting triazole above its melting point of 121° C., and then co-crystallizing the melted triazole with water. Sample A is obtained by cooling the co-crystallized triazole and water in an ambient environment, and then drying under an air vacuum. The mole ratio of water to triazole can be 1:2. Water is added under stirring after the triazole is completely melted into liquid form. By changing the amount of water added during the co-crystallization process, the water ratio in the triazole hydrate can be adjusted. Sample A will have a chemical formula according to formula (I) above.

In another embodiment, a Sample B is prepared by dissolving a large amount of triazole in water above 20° C., and then forming triazole hydrate by crystallization as the temperature of the mixture cools down. The amount of triazole dissolved is larger than that of its solubility at 20° C. In one example, 240 g triazole is dissolved in 120 mL water at 70° C. After the triazole is completely dissolved, the solution is cooled and triazole hydrate crystals are formed by cooling in the ambient environment. Sample B will have a formula matching that of formula (I). Variations of these precise reaction conditions can be made to prepare different triazole hydrate crystals similar to Form B. For example, the amount of triazole can be between 200 g and 240 g, and the temperature at which it is dissolved can be 70° C.+/−10° C.

In another embodiment, a Sample C is prepared by dissolving a large amount of triazole in water above 20° C., and then by forming triazole hydrate through crystallization with water and a doped amount of an alkali as the mixture temperature drops. The amount of triazole dissolved is larger than that of its solubility at 20° C. After the triazole is completely dissolved, an amount of the alkali is added, and the mixture is cooled down to form a triazole hydrate with doped alkali. The term "alkali" here means any substance having a pH>7 for its aqueous solution. In one example, the alkali is ammonium hydroxide. Other alkalis such as potassium hydroxide (KOH), sodium hydroxide (NaOH), lithium hydroxide (LiOH), sodium bicarbonate ($Na_2CO_3$), sodium percarbonate ($NaHCO_3$), potassium carbonate ($K_2CO_3$), potassium percarbonate ($KHCO_3$), salts formed by strong base and weak acid, and other organic bases may also be used for alkali doped triazole preparation. When the alkali is ammonium hydroxide, Sample C will conform to formula (II) above.

In another embodiment, a Sample E is prepared by reacting triazole to an equal mole amount of alkali in aqueous solution. Form E is obtained by evaporating water with heat and then by vacuum. In one example, the alkali is potassium hydroxide. Other alkalis such as ammonium hydroxide, NaOH, LiOH, $Na_2CO_3$, $NaHCO_3$, $K_2CO_3$, $KHCO_3$, salts formed by strong base and weak acid, as well as organic bases could also be used for making a new crystalline form of triazole alkali salt. In this sample, the potassium hydroxide reacts directly to the triazole and forms an alkaline salt, and thus does not conform to any of formulas (I)-(IV) above.

In another embodiment, a Sample F is prepared by melting triazole with temperature above the melting point of 121° C., and then co-crystallizing with water and a doped amount of alkali. In one example, the alkali is potassium hydroxide. It is also evident that other alkalis such as ammonium hydroxide, NaOH, LiOH, $Na_2CO_3$, $NaHCO_3$, $K_2CO_3$, $KHCO_3$, salts formed by strong base and weak acid, as well as organic bases could also be used for alkali doped triazole preparation. Sample F will have a formula according to formula (II) above when the alkali is ammonium hydroxide, or formula (III) when the alkali is potassium hydroxide.

In another embodiment, a Sample G is prepared by dissolving large amount of triazole in water above 20° C., and then by forming triazole hydrate through crystallization with water and doped amount of alkali, as the temperature of the mixture cools down. In one example, the alkali is potassium hydroxide. Other alkalis such as ammonium hydroxide, NaOH, LiOH, $Na_2CO_3$, $NaHCO_3$, $K_2CO_3$, $KHCO_3$, salts formed by a strong base and weak acid, and other organic bases may also be used. Sample G will have formula (III) when the alkali is potassium hydroxide.

In another embodiment, a crystalline form of triazole with an acid co-crystal is formed. The acid may be glycine. The new crystalline form of triazole glycine co-crystal is formed by heating a triazole glycine mixture (with a mole ratio of 7:3) to a first temperature using the DSC instrument (5° C./min from 50 to 150° C., First Run), then keeping isothermal at that first temperature for a first period of time, and rerunning the DSC (5° C./min from 50 to 150° C., Second Run). Different triazole glycine co-crystals could be prepared by changing the ratio of triazole to glycine. It is also evident to one skilled in the art that acid could be any substance having a pH<7 in aqueous solution. Organic or inorganic acids can be used. Glycine is an example of an amino acid suitable for use in the present disclosure. Similarly, other amino acids, for example alanine, could be used. Other organic acids, for example carboxylic acids, may be suitable as well. The first temperature may be from 130° C. to 150° C., inclusive, or any subranges therebetween. In one embodiment, the first period of time is 90 minutes.

Any of the four triazole forms of the present disclosure—hydrates of triazole, triazole alkaline salt, alkali doped triazole, and the triazole acid co-crystal—can be used as active pharmaceutical ingredients for different applications. In addition, triazole can be used as a corrosion inhibitor for chemical mechanical polishing (CMP) applications. The novel triazole forms of the present disclosure may thus be particularly beneficial and suitable for use in CMP slurries, due to the advantages in solubility, stability, and reduced toxicity they provide. For example, the triazole forms of the present disclosure can be used in conjunction with an abrasive, and oxidizer, and a complexing agent in a CMP slurry. The triazole forms of the present disclosure may be the sole corrosion inhibitors in the CMP slurry, or may be used in conjunction with other corrosion inhibitors. As glycine can also be used as a complexing agent, the triazole-glycine co-crystal discussed above may be particularly suitable for use in a CMP slurry.

The abrasives for the CMP slurry can be selected from the group consisting of alumina, fumed silica, colloidal silica, coated particles, titania, ceria, zirconia, or any combinations thereof. The oxidizer can be selected form the group consisting of hydrogen peroxide, ammonium persulfate, silver nitrate (AgNO3), ferric nitrates or chlorides, per acids or salts, ozone water, potassium ferricyanide, potassium dichromate, potassium iodate, potassium bromate, vanadium trioxide, hypochlorous acid, sodium hypochlorite, potassium hypochlorite, calcium hypochlorite, magnesium hypochlorite, ferric nitrate, $KMnO_4$, other inorganic or organic peroxides, or mixtures thereof. The complexing agent can be selected from the group consisting of organic acids and their salts, amino acetic acids, amino acids such as glycine or alanine, carboxylic acids, polyamines, ammonia based compounds, quaternary ammonium compounds, inorganic acids, compounds with both carboxylic and amino functions, such as ethylenediaminetetraacetic acid and diethylene triamine pentaacetic acid, or any mixtures thereof. Suitable corrosion inhibitors may be benzotriazole and its derivatives, tolyl triazole and its derivatives, and azoles, certain surfactants, or any mixtures thereof.

The powder X-ray diffraction patterns (XRD) were obtained by methods known in the art using an X'pert Pro diffractometer from PANalytical. Differential scanning calorimetry was performed on DSC2910 from TA Instrument under helium atmosphere (30 mL/min). Thermogravimetric analysis (TGA) was conducted on TGA2950 from TA Instrument under nitrogen atmosphere (60 mL/min). Micro-Raman solid analysis was studied using a 532 nm excitation laser wavelength.

The following examples are used for illustrating the triazole forms of the present disclosure, and should not be construed as limiting the invention in any way.

EXAMPLE 1

Preparation of Triazole Hydrate 138 g (2 mole) triazole was added to a glass beaker and then heated to 123° C. by using a silicone oil heating bath. After the triazole was completely melted, 18 g (1 mole) DI water was added to the liquid triazole under stirring. After stirring for 5 min, the sample was cooled in an ambient environment. The final product was ground into powder and dried in an air vacuum for 24 h. The sample was characterized by XRD powder diffraction, DSC, TGA and Raman as shown in FIG. 1-a, b, c, d, and e respectively. The triazole hydrate of Example 1 is made according to Sample A above.

EXAMPLE 2

Preparation of Triazole Hydrate 240 g triazole was added to 120 mL water in a 500 mL beaker under stirring. The temperature was heated to 70° C. to completely dissolve the triazole. The stirring was kept for 10 min after the triazole is completely dissolved. The sample was cooled in an ambient environment, and triazole hydrate crystal was formed during the cooling of the mixture. Triazole hydrate was dried by an air vacuum to remove absorbed water. The sample was further characterized by XRD powder diffraction, DSC, TGA and Raman as shown in FIG. 2-a, b, c, d and e respectively. The triazole hydrate of Example 2 is made according to Sample B above.

EXAMPLE 3

Preparation of Ammonium Hydroxide Doped Triazole Hydrate 200 g triazole was added to 100 mL water in a beaker under stirring. The sample was heated to 65° C. so that triazole was completely dissolved. 5 g 29% ammonium hydroxide was added to the triazole solution under stirring. The sample was then cooled in an ambient environment for crystallization. Triazole hydrate with doped ammonium hydroxide was formed during the crystallization process. The sample was filtered and dried under air vacuum. The sample is further characterized by XRD powder diffraction, DSC, TGA, and Raman as shown in FIG. 3-a, b, c, d and e respectively. The triazole hydrate of Example 3 is made according to Sample C above.

EXAMPLE 4

Preparation of Triazole Potassium Salt Hydrate 138 g (2 mole) triazole was dissolved in 400 mL water in a beaker. 649 g 17.3% g potassium hydroxide (pure KOH: 2 mole) was added to triazole solution under stirring. The reaction continued for 2 h under stirring. The solid sample was obtained by heat evaporating water and then dried by an air pump. The sample is further characterized by XRD powder diffraction, DSC, and Raman as shown in FIG. 5-a, b and c respectively. The triazole hydrate of Example 4 is made according to Sample E above.

EXAMPLE 5

Preparation of KOH Doped Triazole Hydrate 138 g (2 mole) triazole is added to a 500 mL beaker and then heated to 123° C. by using a silicone oil heating bath. After the triazole was completely melted, 19 g of 3.63% KOH was added to the liquid triazole under stirring. After stirring for 5 min, the sample was cooled in the ambient environment. The final product was ground into powder and dried by air vacuum for 24 h. The sample was characterized by XRD powder diffraction, DSC and Raman as shown in FIG. 5-a, b, c and d respectively. The triazole hydrate of Example 5 is made according to Sample F above.

EXAMPLE 6

Preparation of KOH Doped Triazole Hydrate 240 g triazole was added to 108 mL water in a beaker under stirring. The sample was heated to 70° C. so that triazole was completely dissolved. 12 g 10% KOH was added to the triazole solution under stirring. After heating for 10 min, the sample was cooled in an ambient environment. KOH doped triazole hydrate crystal was formed during a cooling process. The solid was separated by filtration and further dried under an air vacuum. The sample was characterized by XRD powder diffraction, DSC and Raman as shown in FIG. 6-a, b, c and d respectively. The triazole hydrate of Example 6 is made according to Sample G above.

EXAMPLE 7

Figure 7:
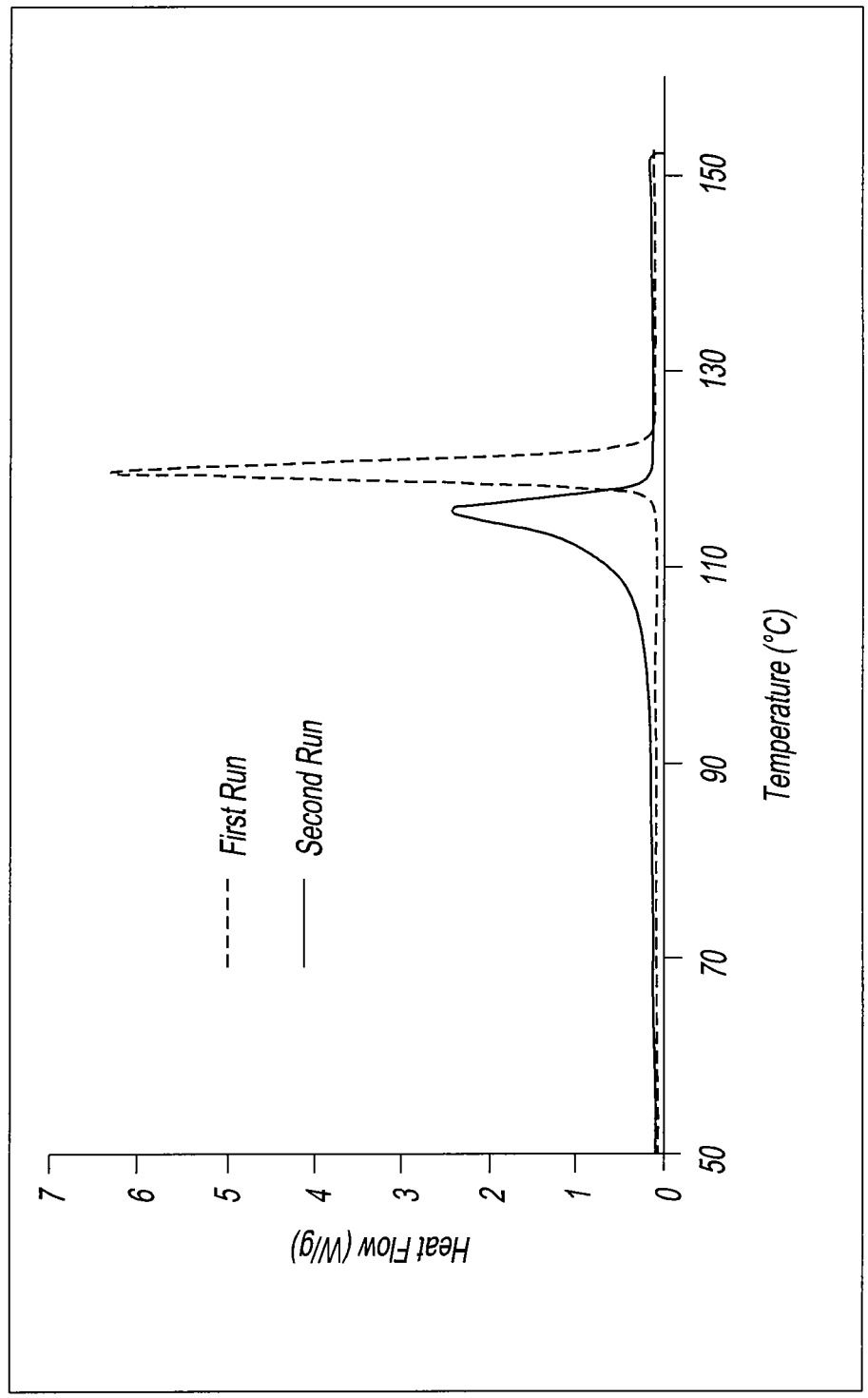
FIG. 7 shows DSC curves of the 1,2,4-triazole glycine mixture (first run, dashed line) and the 1,2,4-triazole glycine co-crystal (second run, solid line) described in Example 7.

Preparation of Triazole Glycine Co-Crystal 3.66 mg of a triazole glycine mixture (mole ratio: 7:3) was sealed in an aluminum pan for DSC measurements. The triazole glycine mixture was first heated to 150° C. (above the melting point of 1,2,4-triazole) and measured the DSC as the first run (5° C./min from 50 to 150° C.) as shown in FIG. 7 by the dashed line. The sample was held at 150° C. for 90 min so that glycine was soaked in melted triazole solution. Then the sample was cooled to 20° C. and rerun under the DSC test (the second run, 5° C./min from 50 to 150° C.) as shown in FIG. 7 by the solid line. In FIG. 7, the peak temperature decreased from 120 to 115° C. as from the First Run to the Second Run indicating that the triazole glycine co-crystal had formed.

Table 1 below summarizes the major XRD peaks for Samples A-C, and E-G, as shown in the Figures. As can be seen, Samples A-C, F, and G have similar if not identical XRD profiles. In Sample E, because the potassium hydroxide reacted directly with the triazole, the XRD profile was completely different than in the other structures.

of pure 1,2,4-triazole) and asymmetric band shape, indicating the hydrate formed in Sample A. The thermogravimetric analysis (TGA) and derivative TGA in FIG. 1-d show a two-step weight loss, which implies that the crystal Sample A contains hydrate water in the structure. Sample A also has significant Raman bands as depicted in FIG. 1-e at 58 $cm^{-1}$, 76 $cm^{-1}$, 104 $cm^{-1}$, 157 $cm^{-1}$, 924 $cm^{-1}$, 962 $cm^{-1}$, 985 $cm^{-1}$, 1067 $cm^{-1}$, 1152 $cm^{-1}$, 1187 $cm^{-1}$, 1267 $cm^{-1}$, 1307 $cm^{-1}$, 1365 $cm^{-1}$, 1384 $cm^{-1}$, 1486 $cm^{-1}$, 2830 $cm^{-1}$ (broad band 2500 to 3012 $cm^{-1}$), 3029 $cm^{-1}$, and 3129 $cm^{-1}$. The broad band from 2500 to 3012 $cm^{-1}$ might be associated with the hydrate formation.

FIG. 2-c shows a DSC plat of Sample B having an onset temperature of 117.4° C., larger than that of Sample A. The TGA and derivative TGA plots in FIG. 2-d show a two-step weight loss indicating that the crystal Sample B contains hydrate water in the structure. Sample B has significant Raman bands as depicted in FIG. 2-e at 61 $cm^{-1}$, 79 $cm^{-1}$, 108 $cm^{-1}$, 164 $cm^{-1}$, 189 $cm^{-1}$, 885 $cm^{-1}$, 927 $cm^{-1}$, 962 $cm^{-1}$, 985 $cm^{-1}$, 1067 $cm^{-1}$, 1152 $cm^{-1}$, 1267 $cm^{-1}$, 1307 $cm^{-1}$, 1365 $cm^{-1}$, 1384 $cm^{-1}$, 2815 $cm^{-1}$ (broad band 2500 to 3012 $cm^{-1}$), 3029 $cm^{-1}$, and 3126 $cm^{-1}$. The broad band from 2500 to 3012 $cm^{-1}$ might be associated with the hydrate formation.

The DSC plot of Sample C shown in FIG. 3-c has an onset temperature of 115.56° C. and asymmetric band shape. The TGA and derivative TGA plots of Sample C in FIG. 3-d show a two-step weight loss indicating the presence of hydrate. The Raman plot of Sample C shown in FIG. 3-e has significant Raman bands at 61 $cm^{-1}$, 83 $cm^{-1}$, 122 $cm^{-1}$, 160 $cm^{-1}$, 189 $cm^{-1}$, 656 $cm^{-1}$, 682 $cm^{-1}$, 885 $cm^{-1}$, 962 $cm^{-1}$, 981 $cm^{-1}$, 1064 $cm^{-1}$, 1152 $cm^{-1}$, 1186 $cm^{-1}$, 1264 $cm^{-1}$, 1304 $cm^{-1}$, 1384 $cm^{-1}$, 1486 $cm^{-1}$, 2794 $cm^{-1}$ (broad band 2500 to 3012 $cm^{-1}$), 3026 $cm^{-1}$, and 3131 $cm^{-1}$. The broad band from 2500 to 3012 $cm^{-1}$ might be associated with the hydrate formation.

Figure 4A:
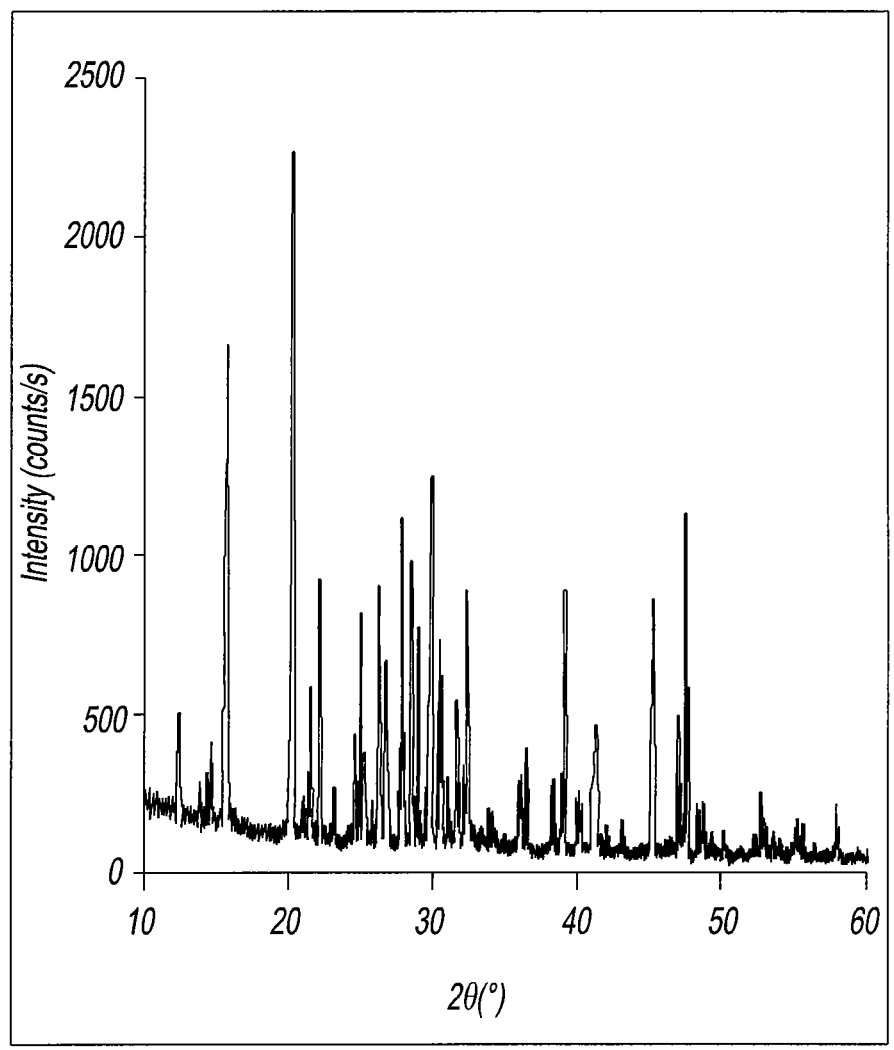
FIG. 4-a shows an XRD spectrum of the 1,2,4-triazole potassium salt hydrate sample described in Example 4.
Figure 4B:
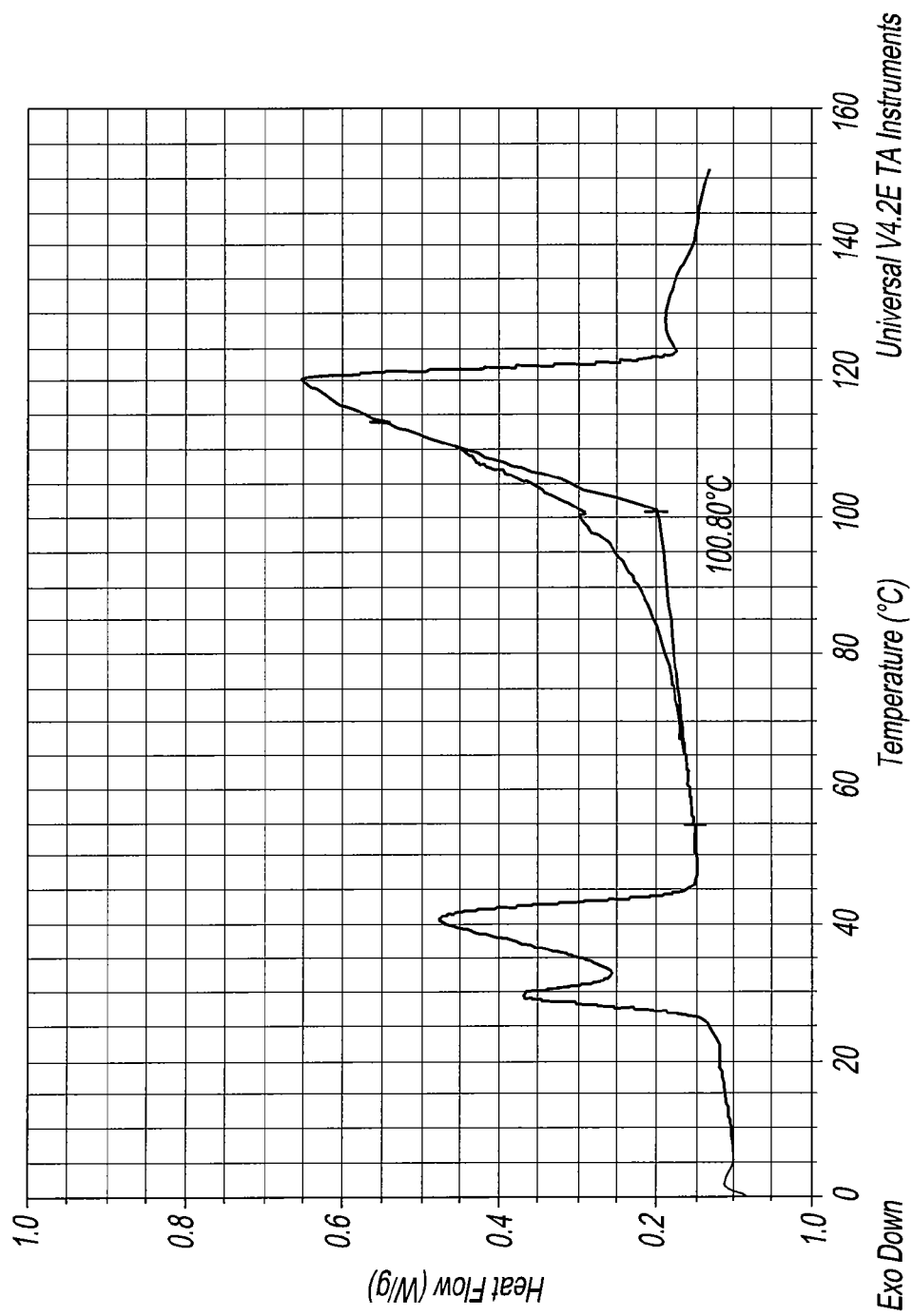
Figure 4C:
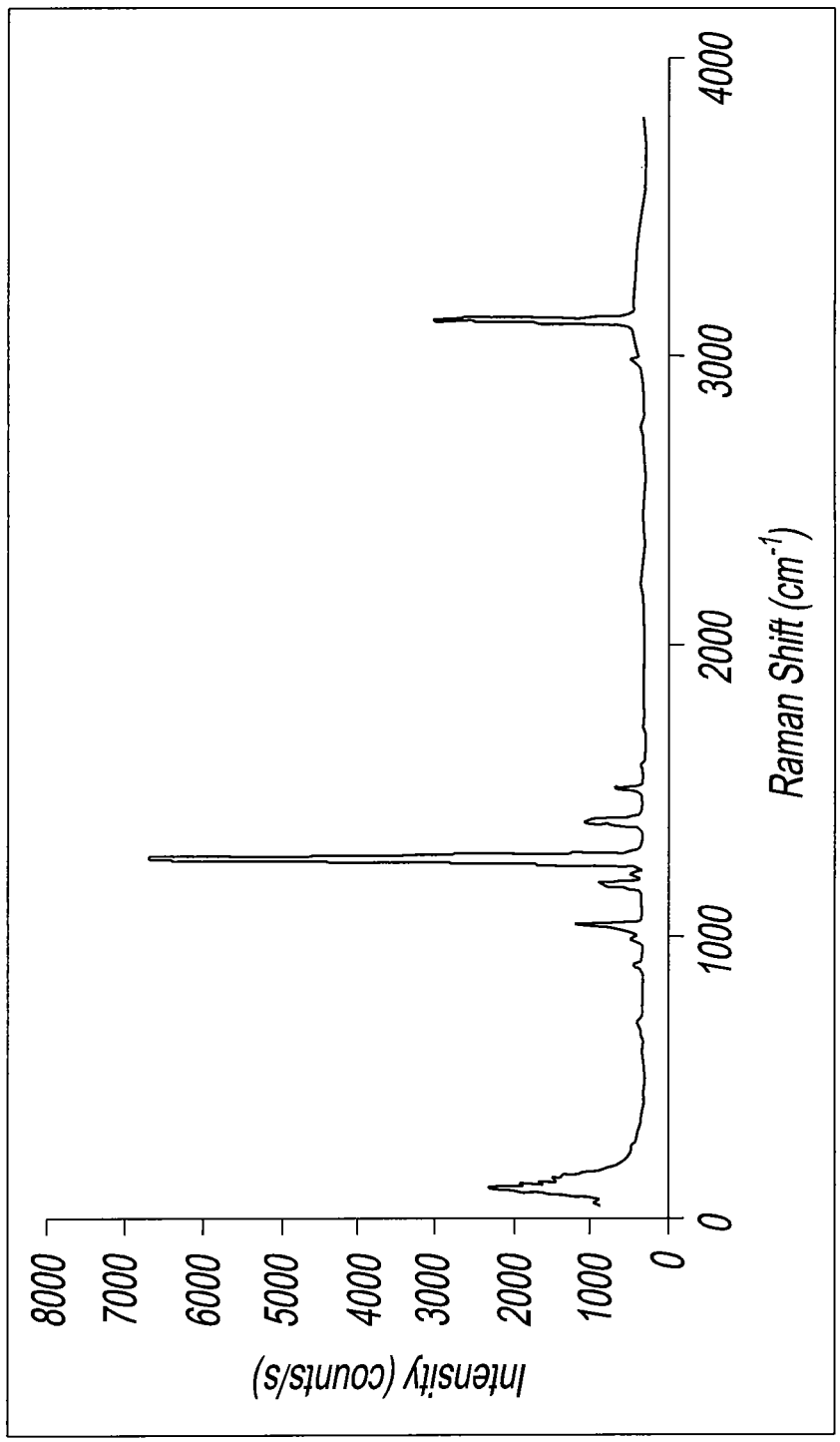
Figure 5A:
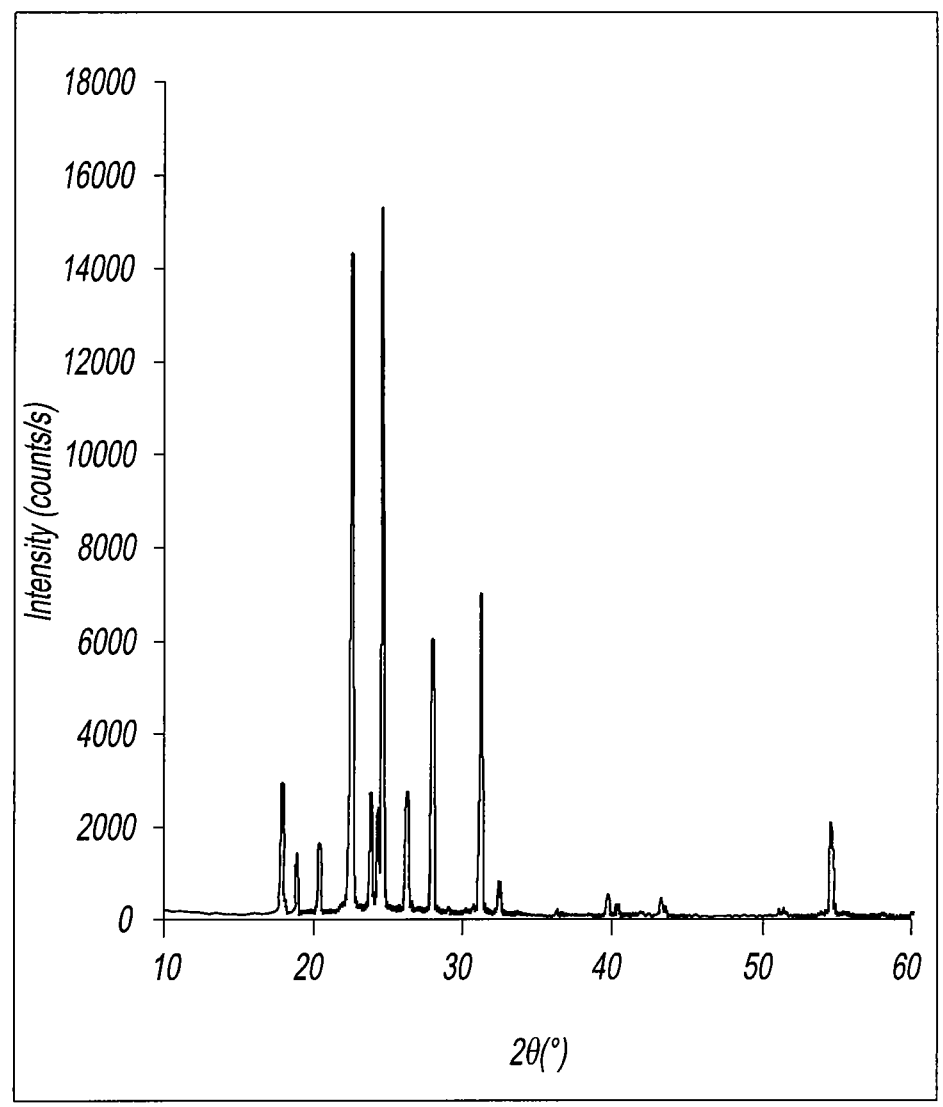
FIG. 5-a shows an XRD spectrum of the potassium hydroxide (KOH) doped 1,2,4-triazole hydrate sample described in Example 5.
Figure 5B:
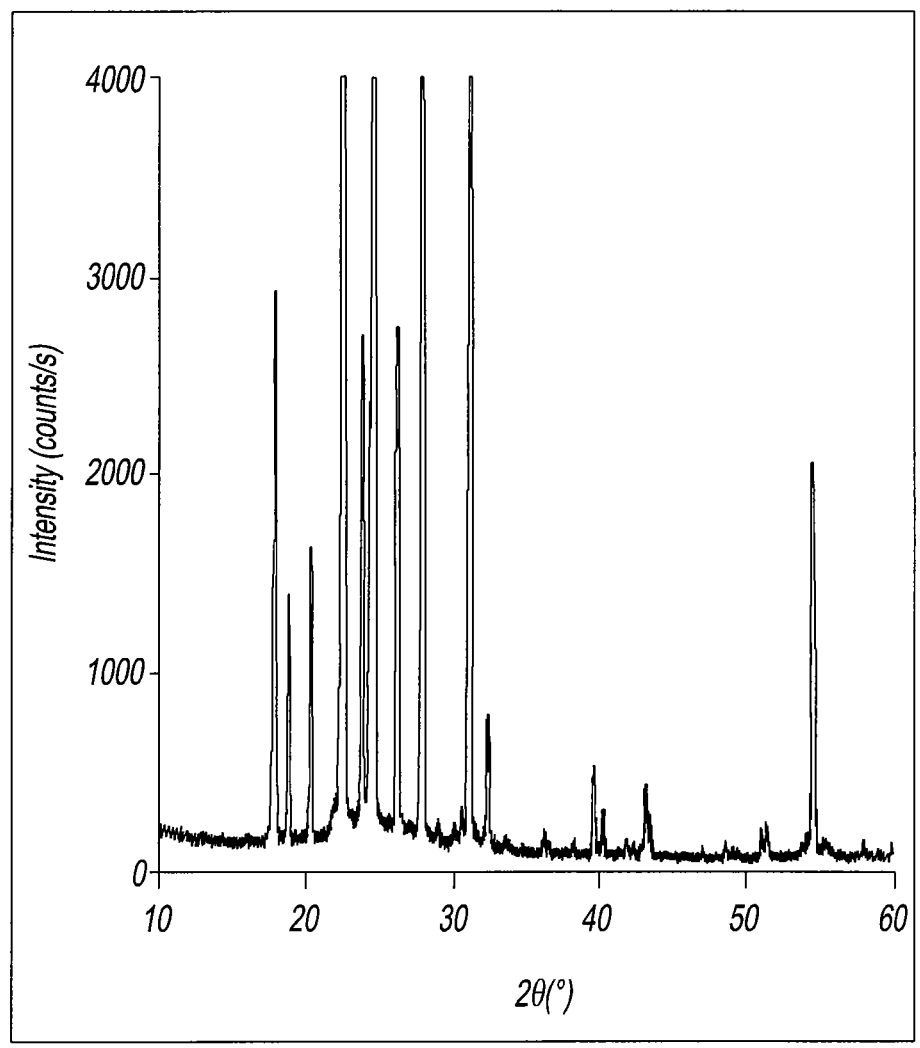
Figure 5C:
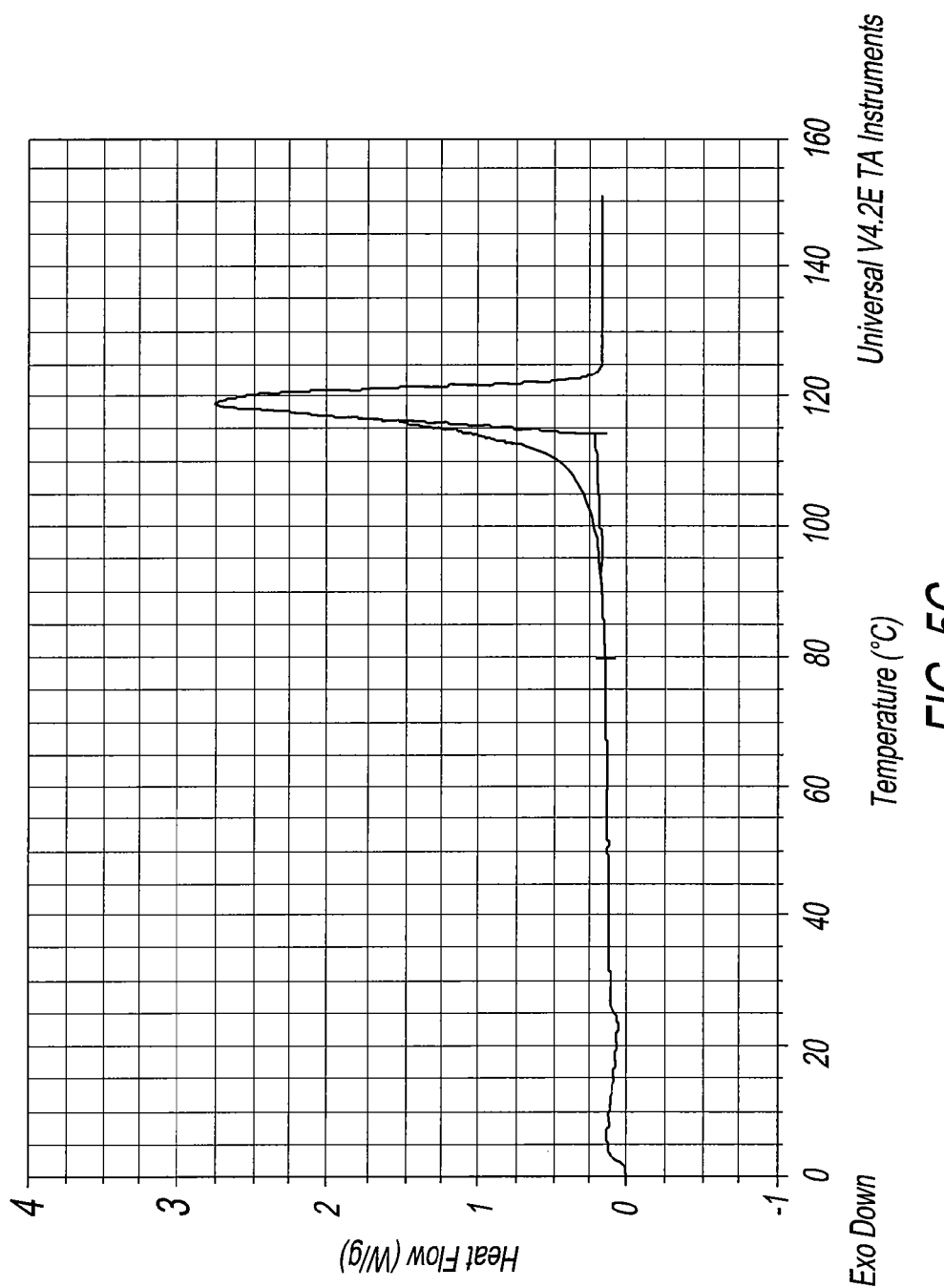
Figure 5D:
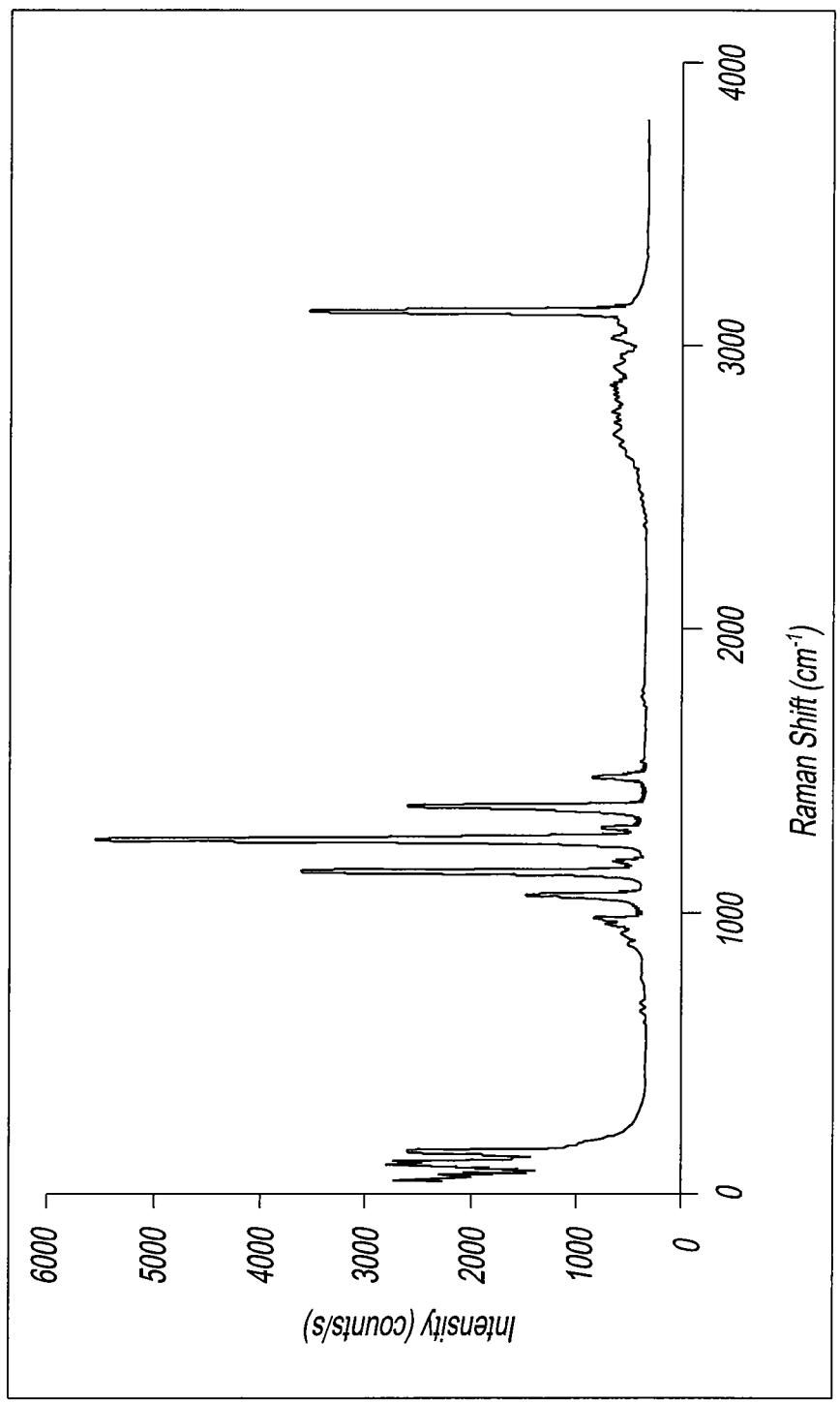
Figure 6A:
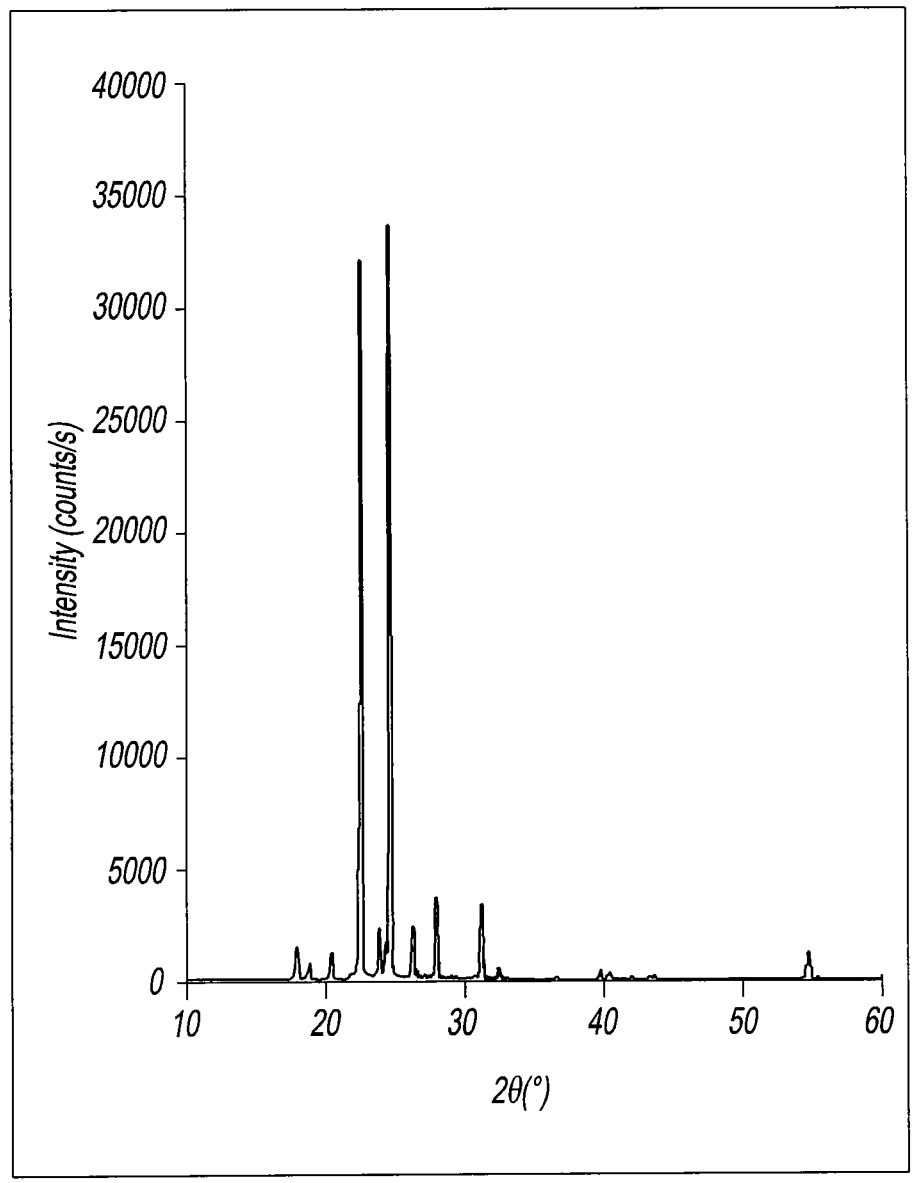
FIG. 6-a shows an XRD spectrum of the KOH doped 1,2,4-triazole hydrate sample described in Example 6.
Figure 6B:
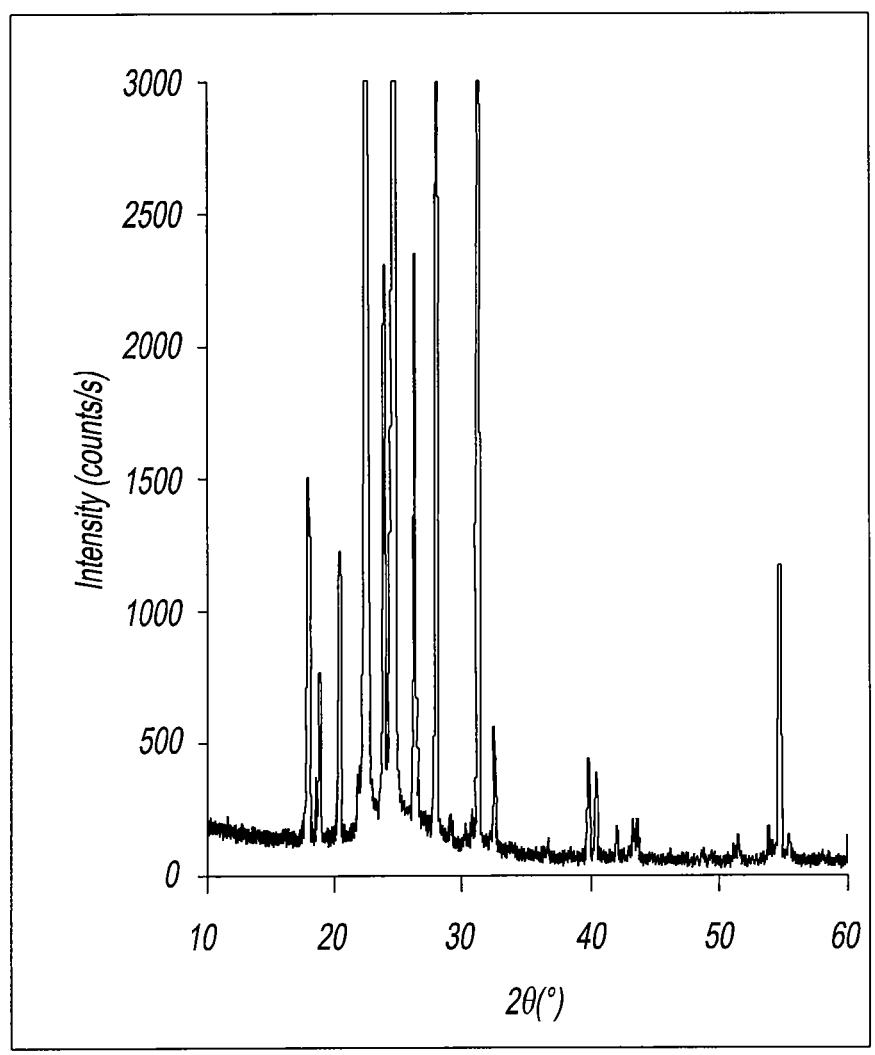
Figure 6C:
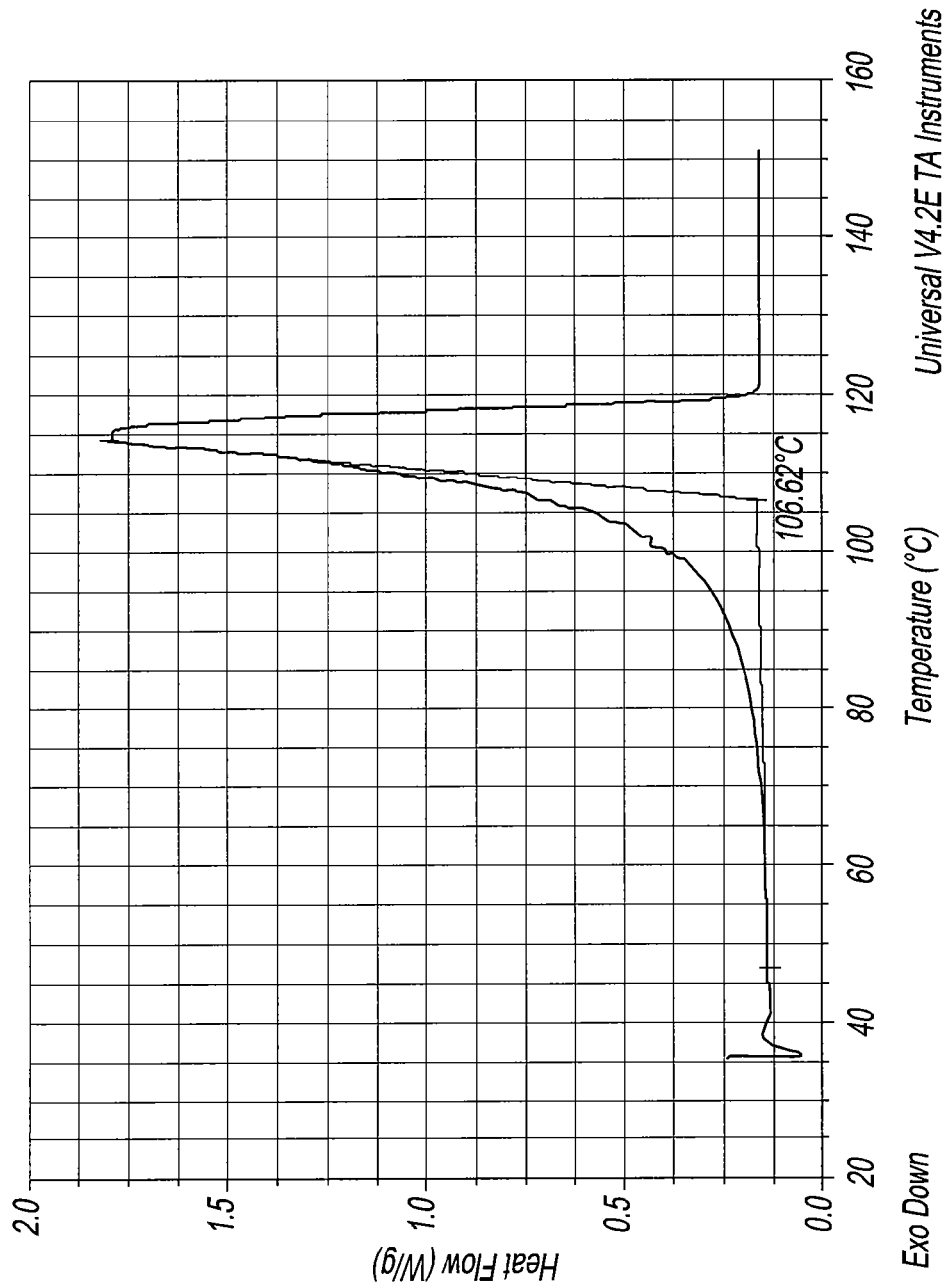
Figure 6D:
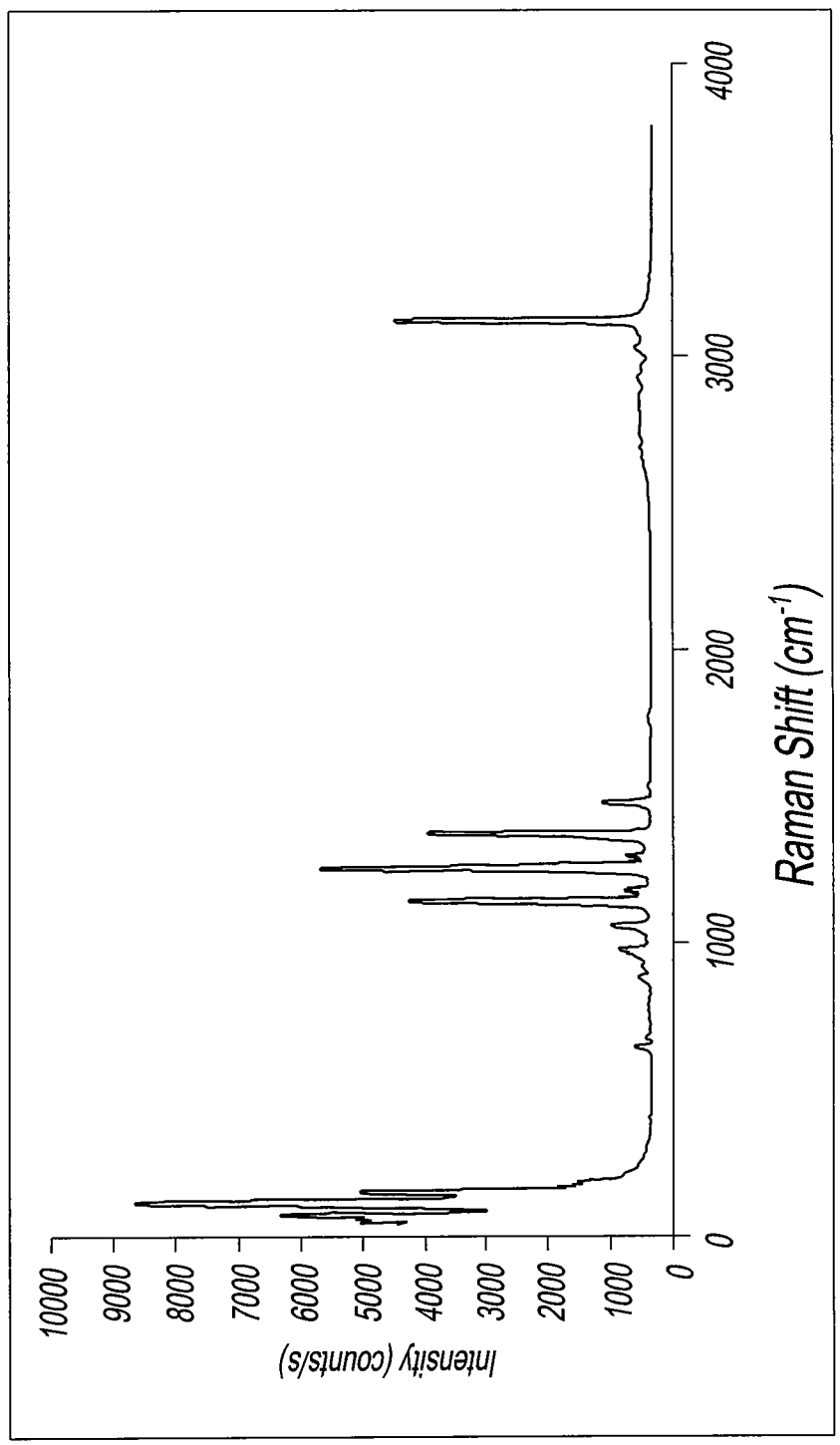

The DSC plot of Sample E as shown in FIG. 4-b shows an onset temperature of 100.8° C. and an asymmetric band. Sample E has significant Raman bands as shown in FIG. 4-c at 109 $cm^{-1}$, 137 $cm^{-1}$, 148 $cm^{-1}$, 873 $cm^{-1}$, 966 $cm^{-1}$, 1011 $cm^{-1}$, 1156 $cm^{-1}$, 1246 $cm^{-1}$, 1371 $cm^{-1}$, 1483 $cm^{-1}$, 2964 $cm^{-1}$, and 3106 $cm^{-1}$.

| Sample | A | B | C | E | F | G |
|---|---|---|---|---|---|---|
| Main Peaks | 17.9 ± 0.2 | 18 ± 0.2 | 17.9 ± 0.2 | 12.4 ± 0.2 | 17.9 ± 0.2 | 17.9 ± 0.2 |
| | 18.9 ± 0.2 | 19 ± 0.2 | 18.9 ± 0.2 | 13.9 ± 0.2 | 18.82 ± 0.2 | 18.8 ± 0.2 |
| | 20.4 ± 0.2 | 20.4 ± 0.2 | 20.5 ± 0.2 | 14.7 ± 0.2 | 20.3 ± 0.2 | 20.4 ± 0.2 |
| | 22.6 ± 0.2 | 22.6 ± 0.2 | 22.5 ± 0.2 | 15.7 ± 0.2 | 22.56 ± 0.2 | 22.6 ± 0.2 |
| | 23.9 ± 0.2 | 23.9 ± 0.2 | 23.9 ± 0.2 | 20.3 ± 0.2 | 23.8 ± 0.2 | 23.8 ± 0.2 |
| | 24.7 ± 0.2 | 24.7 ± 0.2 | 24.7 ± 0.2 | 22.23 ± 0.2 | 24.3 ± 0.2 | 24.3 ± 0.2 |
| | 26.3 ± 0.2 | 26.3 ± 0.2 | 26.3 ± 0.2 | 22.9 ± 0.2 | 24.6 ± 0.2 | 24.6 ± 0.2 |
| | 28 ± 0.2 | 28 ± 0.2 | 28 ± 0.2 | 24.84 ± 0.2 | 26.2 ± 0.2 | 26.3 ± 0.2 |
| | 31.3 ± 0.2 | 31.3 ± 0.2 | 31.37 ± 0.2 | 26.28 ± 0.2 | 27.9 ± 0.2 | 28 ± 0.2 |
| | 32.4 ± 0.2 | 32.5 ± 0.2 | 32.5 ± 0.2 | 26.4 ± 0.2 | 31.2 ± 0.2 | 31.2 ± 0.2 |
| | 39.8 ± 0.2 | 39.8 ± 0.2 | 39.8 ± 0.2 | 27.8 ± 0.2 | 32.4 ± 0.2 | 32.5 ± 0.2 |
| | 40.3 ± 0.2 | 40.4 ± 0.2 | 40.4 ± 0.2 | 28 ± 0.2 | 39.7 ± 0.2 | 39.79 ± 0.2 |
| | 43.3 ± 0.2 | 43.3 ± 0.2 | 43.3 ± 0.2 | 28.5 ± 0.2 | 43.2 ± 0.2 | 54.7 ± 0.2 |
| | 54.6 ± 0.2 | 54.7 ± 0.2 | 54.75 ± 0.2 | 29.85 ± 0.2 | 54.5 ± 0.2 | |
| | | | | 30.6 ± 0.2 | | |
| | | | | 31.6 ± 0.2 | | |
| | | | | 32.54 ± 0.2 | | |
| | | | | 36 ± 0.2 | | |
| | | | | 36.5 ± 0.2 | | |
| | | | | 39.1 ± 0.2 | | |
| | | | | 45.3 ± 0.2 | | |
| | | | | 47.5 ± 0.2 | | |

The differential scanning calorimetry (DSC) plot in FIG. 1-c shows an onset temperature of 105.6° C. (lower than that Sample F has a DSC onset temperature at 114.3° C. and asymmetric band in FIG. 5-c. Sample F has significant Raman bands as shown in FIG. 5-*d* at 52 m$^{-1}$, 70 cm$^{-1}$, 112 cm$^{-1}$, 155 cm$^{-1}$, 647 cm$^{-1}$, 879 cm$^{-1}$, 956 cm$^{-1}$, 976 cm$^{-1}$, 1061 cm$^{-1}$, 1146 cm$^{-1}$, 1181 ccm$^{-1}$, 1258 cm$^{-1}$, 1298 cm$^{-1}$, 1378 cm$^{-1}$, 1480 cm$^{-1}$, 2778 cm$^{-1}$ (broad band 2500 to 2993 cm$^{-1}$), 3025 cm$^{-1}$, and 3125 cm$^{-1}$. The broad band from 2500 to 2993 cm$^{-1}$ might be associated with the hydrate formation.

Sample G has a DSC onset temperature of 106.6° C. and asymmetric band in FIG. 6-*c*. The Raman profile of Sample G shows significant bands at as shown in FIG. 6-*d*.

While the present disclosure has been described with reference to one or more particular embodiments, it will be understood by those skilled in the art that various changes may be made and equivalents may be substituted for elements thereof without departing from the scope thereof. In addition, many modifications may be made to adapt a particular situation or material to the teachings of the disclosure without departing from the scope thereof. Therefore, it is intended that the disclosure not be limited to the particular embodiment(s) disclosed as the best mode contemplated for carrying out this disclosure.

What is claimed is:

1. A hydrate of an alkali doped 1,2,4-triazole, having the following formula:

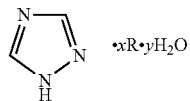

wherein R is an alkali group, and wherein x and y are integers, or fractions thereof.

2. The hydrate of claim 1, wherein R is an alkali group.

3. The hydrate of claim 2, wherein said alkali group is selected from the group consisting of ammonium hydroxide, potassium hydroxide, sodium hydroxide, lithium hydroxide, sodium bicarbonate, sodium percarbonate, potassium carbonate, and potassium percarbonate.

4. The hydrate of claim 3, wherein said alkali group is ammonium hydroxide or potassium hydroxide.

5. The hydrate of claim 1, wherein x is a fraction less than 1.

6. The hydrate of claim 5, wherein R is an alkali group selected from the group consisting of ammonium hydroxide, potassium hydroxide, sodium hydroxide, lithium hydroxide, sodium bicarbonate, sodium percarbonate, potassium carbonate, and potassium percarbonate.

7. A hydrate of an alkali doped 1,2,4-triazole, having the following formula:

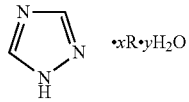

wherein R is potassium hydroxide, and wherein x and y are integers, or fractions thereof.

8. The hydrate of claim 7, wherein x is a fraction less than 1.

* * * * *